(12) United States Patent
Anderson et al.

(10) Patent No.: US 6,270,990 B1
(45) Date of Patent: *Aug. 7, 2001

(54) NEURON-RESTRICTIVE SILENCER FACTOR PROTEINS

(75) Inventors: David J. Anderson, Altadena, CA (US); Christopher J. Schoenherr, Princeton, NJ (US)

(73) Assignee: California Institute of Technology, Pasadena, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/894,997

(22) PCT Filed: Mar. 1, 1996

(86) PCT No.: PCT/US96/02817

§ 371 Date: Jan. 16, 1998

§ 102(e) Date: Jan. 16, 1998

(87) PCT Pub. No.: WO96/27665

PCT Pub. Date: Sep. 12, 1996

Related U.S. Application Data

(63) Continuation-in-part of application No. 08/398,590, filed on Mar. 3, 1995, now Pat. No. 5,935,811.

(51) Int. Cl.[7] ............................ C07H 21/04; C12P 21/06; C07K 14/47; C12N 15/63
(52) U.S. Cl. ..................... 435/69.1; 435/320.1; 435/325; 530/350; 536/23.1; 536/23.5
(58) Field of Search ............................... 435/69.1, 320.1, 435/325; 530/350; 536/23.1, 23.5

(56) References Cited

U.S. PATENT DOCUMENTS 5,817,617 * 10/1998 Tuomanen et al. .

FOREIGN PATENT DOCUMENTS

96/29433   9/1996  (WO) .

OTHER PUBLICATIONS

Schoenherr et al., "Mouse Neural Restrictive Silencer Factor," *EMBL*, Accession No. Mm 13878 (Jul. 1, 1995).
Krieg et al., "Gene Activation in Response to Response to Neural Induction," *Cellular and Molecular Biology Research*, 39:377–383 (1993).
Sauerwald et al., "The 5'–Flanking Region of the Synapsin I Gene—A G+C–Rich, TATA– and CAAT–Less, Phylogenetically Conserved Sequence with Cell Type–specific Promoter Function," *J. Biol. Chem.*, 265(25):14932–14937 (1990).
Vandenbergh, D.J., et al., "Chromatin structure as a molecular marker of cell lineage and developmental potential in neural crest–derived chromaffin cells", *Neuron*, 3:507–518, (1989).
Stein, R., et al., "The NGF–Inducible SCG10 mRNA Encodes a Novel Membrane–Bound Protein Present in Growth Cones and Abundant in Developing Neurons", *Neuron*, 1:463–476 (1988).
Wuenschell, C.W., et al., "Analysis of SCG10 Gene Expression in Transgenic Mice Reveals that Neural Specificity Is Achieved through Selective Derepression", *Neuron*, 4:595–602 (1990).
Mori, N., et al., "A Cell Type–Preferred Silencer Element That Controls the Neural–Specific Expression of the SCG10 Gene", *Neuron*, 4:583–594, (1990).
Schoenherr, C.J., et al., "The Neuron–Restrictive Silencer Factor (NRSF): A Coordinate Repressor of Multiple Neuron–Specific Genes", *Science*, 267:1360–1363 (1995).
Maue, R.A., et al., "Neuron–Specific Expression of the Rat Brain Type II Sodium Channel Gene Is Directed by Upstream Regulatory Elements", *Neuron*, 4:223–231 (1990).
Kraner, S.D., et al., "Silencing the Type II Sodium Channel Gene: A Model for Neural–Specific Gene Regulation", *Neuron*, 9:37–44, (1992).
Chong, J.A., et al., "REST: A Mammalian Silencer Protein That Restricts Sodium Channel Gene Expression to Neurons," *Cell*, 80:949–957 (1995).
Mori, N., et al., "A Common Silencer Element in the SCG10 and Type II Na+Channel Genes Binds a Factor Present in Nonneuronal Cells but Not in Neuronal Cells", *Neuron*, 9:45–54 (1992).
Reeck et al., "'Homology' in Proteins and Nucleic Acids: A Terminology Muddle and a Way Out of It," *Cell* 50:667 (1987).
Chowdhury et al., "Specific and Ubiquitous Expression of Different Zn Finger Protein Genes in the Mouse," *Nucleic Acids Research*, 16(21):9995–10011 (1988).

* cited by examiner

*Primary Examiner*—Gary L. Kunz
*Assistant Examiner*—Stephen Gucker
(74) *Attorney, Agent, or Firm*—Mintz, Levin, Cohn, Ferris, Glovsky and Popeo, P.C.; Ivor R. Elrifi

(57) ABSTRACT

The present invention relates to neuron-restrictive silencer factor proteins, nucleic acids, and antibodies thereto.

5 Claims, 19 Drawing Sheets

NRSEs present in neuronal genes

| CONSENSUS: | TTCAGCACChCGGAGAGnGCC | | Intragenic Position |
|---|---|---|---|
| SOG10 | GCCAT | ----------------- | TCTGC | 5' Regulatory |
| Na CHANNEL | TGGGT | -----A-------C--A-- | AGAGT | 5' Regulatory |
| SYNAPSIN I | CCAGC | ----------------- | TTOGC | 5' Regulatory |
| BDNF | GTCCA | ----------T-------- | AGOGG | 1st Intron |
| GLYCINE RECEPTR (rev) | GGOGT | ----------------T-- | CAGAC | 5' UTR |
| NMDA RECEPTOR | CCCGC | ----------------- | GGCCG | 5' UTR |
| ACH RECPTR B2 | GCGGC | ----------------- | CCACC | 5' UTR |
| NEUROFILIMANE-M | GGGGT | ----------T-------- | GGCCG | 5' Regulatory |
| B-4 TUBLIN | CGCCG | ----------------- | GCCTG | 1st Intron |
| CORT. RELEASING FCTR | GGCGC | ----------------- | CCTCC | 1st Intron |
| CALBINDIN | GCACA | G--------------- | CCCGC | 5' UTR |
| SYNAPTOTAGMIN-4 | GTTCT | ----------------A | CGCAG | 5' UTR |
| HES-3 | GGGCA | GG--------T-------- | AACCC | Coding region |
| SYNAPTOPHYSIN | CGOGC | -C-------T-------- | CGGOG | 1st Intron |

FIG._1A

Evolutionary conservation of NRSEs

| HUMAN CALBINDIN | AG-------A---- | |
|---|---|---|
| CHICKEN CALBINDIN | G--------------- | |
| RAT CALBINDIN | AG--------------- | |
| MOUSE CALBINDIN | AG--------------- | |
| HUMAN CRF: | | |
| RAT CRF | ----------------- | |
| SHEEP CRF | --------T-------- | 5' UTR |
| XENOPUS CRF | ----------------AA | |
| HUMAN NEURONAL NIC ACHR B-2 | -------------T-- | 1st Intron |
| RAT NEURONAL NIC ACHR B-2 | --------T-------- | |
| HUMAN NMDAR (NR1-1) | ----------------- | 5' UTR |
| RAT NMDAR (NR1-1) | ----------AT-- | |
| HUMAN SYNAPSIN I | ----------------- | 5' UTR |
| RAT SYNAPSIN I | --T--T----------- | 5' Regulatory |

NRSEs in non-neuronal genes

| | | | | |
|---|---|---|---|---|
| SOM. ACT. FCTR. (rev) | GTTCT | ------------A | CGCAG | 5' UTR |
| NCAM | GCGAT | -------G----AA | CCTGG | 1st Intron |
| ATRIAL NATRIURETIC PEPTIDE | TAAAC | ------A----CG- | CGAGG | 3' UTR |
| RAT APRT (rev) | GCTGA | G----G----T--- | TGACC | Intron |
| BOVINE P-450 (rev) | AGTTC | ------G----T--- | AGGGT | Intron |
| CANINE DISTEMPER VIRUS (rev) | TGTCT | ---C-T-----G--- | AGAGT | Coding region |
| SHEEP KERATIN | ATGTG | A---------G--- | ATGAG | 5' Regulatory |
| MOUSE SKELETAL ACTIN (rev) | GCTTC | GG--------C--- | GCCAG | 3' Regulatory |
| T-CELL RECEPTOR BETA | GTACC | G----A--T----- | TGACA | Coding Region |
| PIG LACTALBUMIN (rev) | TGTCT | -----------T-A | CATTT | Coding Region |

FIG._2

Transcriptional Repression by λHZ4

| Reporter Plasmid | pCMV-HZ4 | Percent CAT activity | Fold repression |
|---|---|---|---|
| pCAT3-S36++ | 0 µg | 100 | - |
| | 1 | 8.3 ± 0.6 | 11.4 |
| | 4 | 3.1 ± 0.3 | 32 |
| pCAT3 | 0 | 100 | - |
| | 1 | 77 ± 0.8 | 1.3 |
| | 4 | 67.5 ± 3.8 | 1.5 |

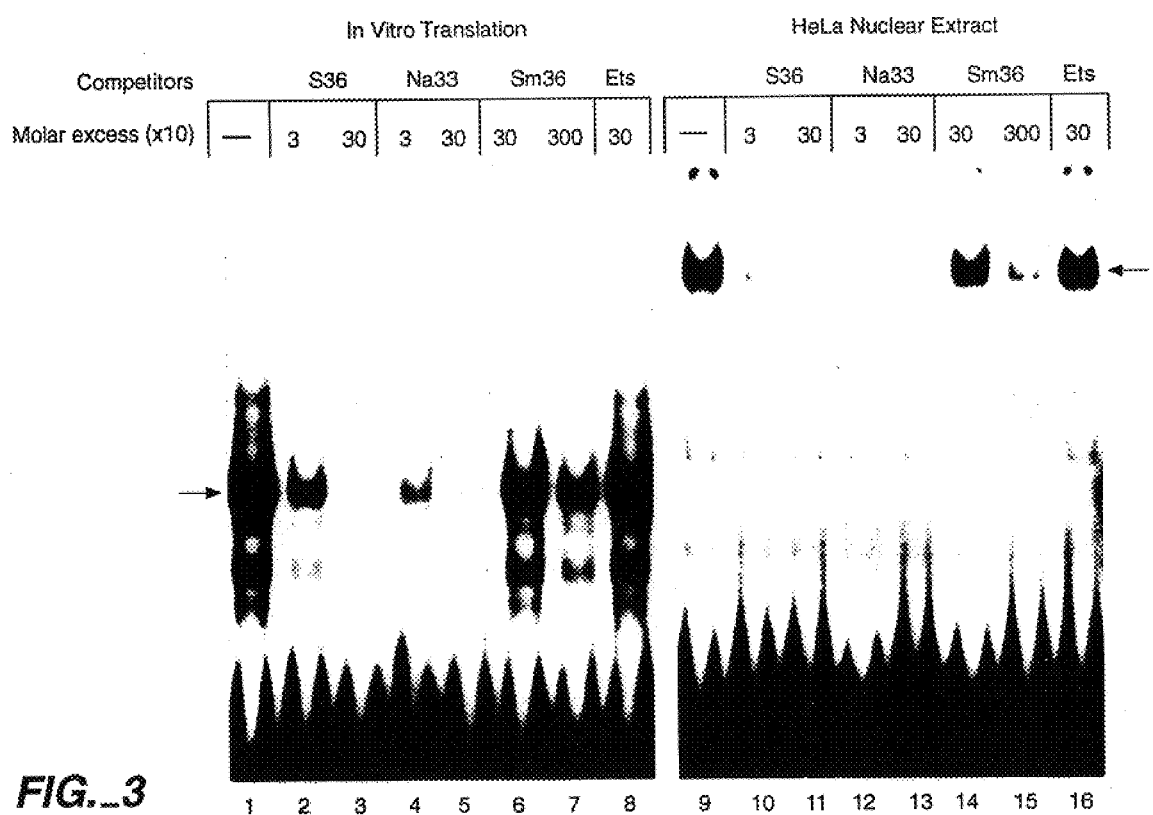
FIG._3

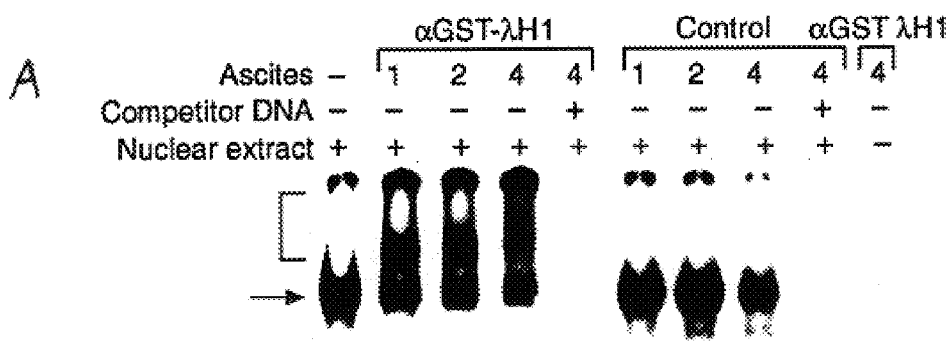
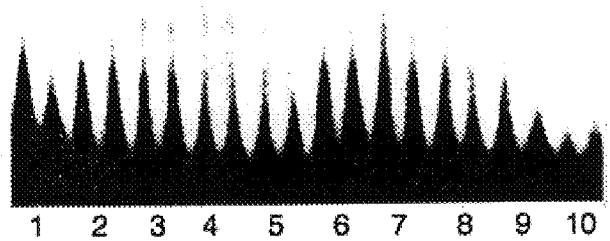
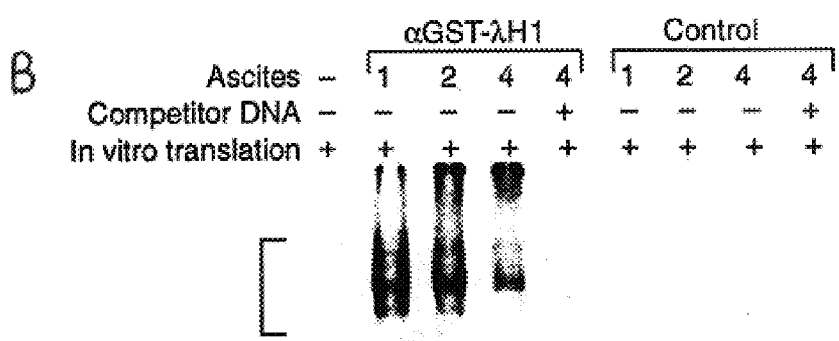
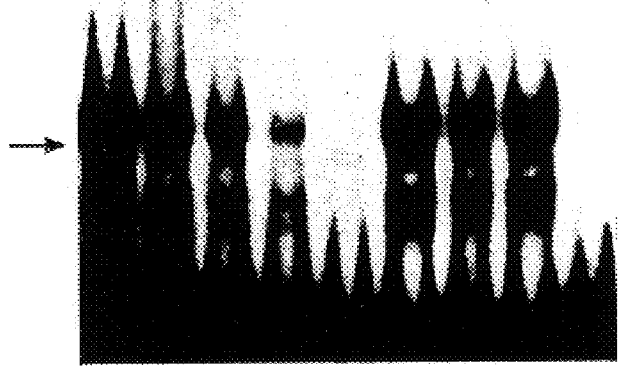
FIG._4

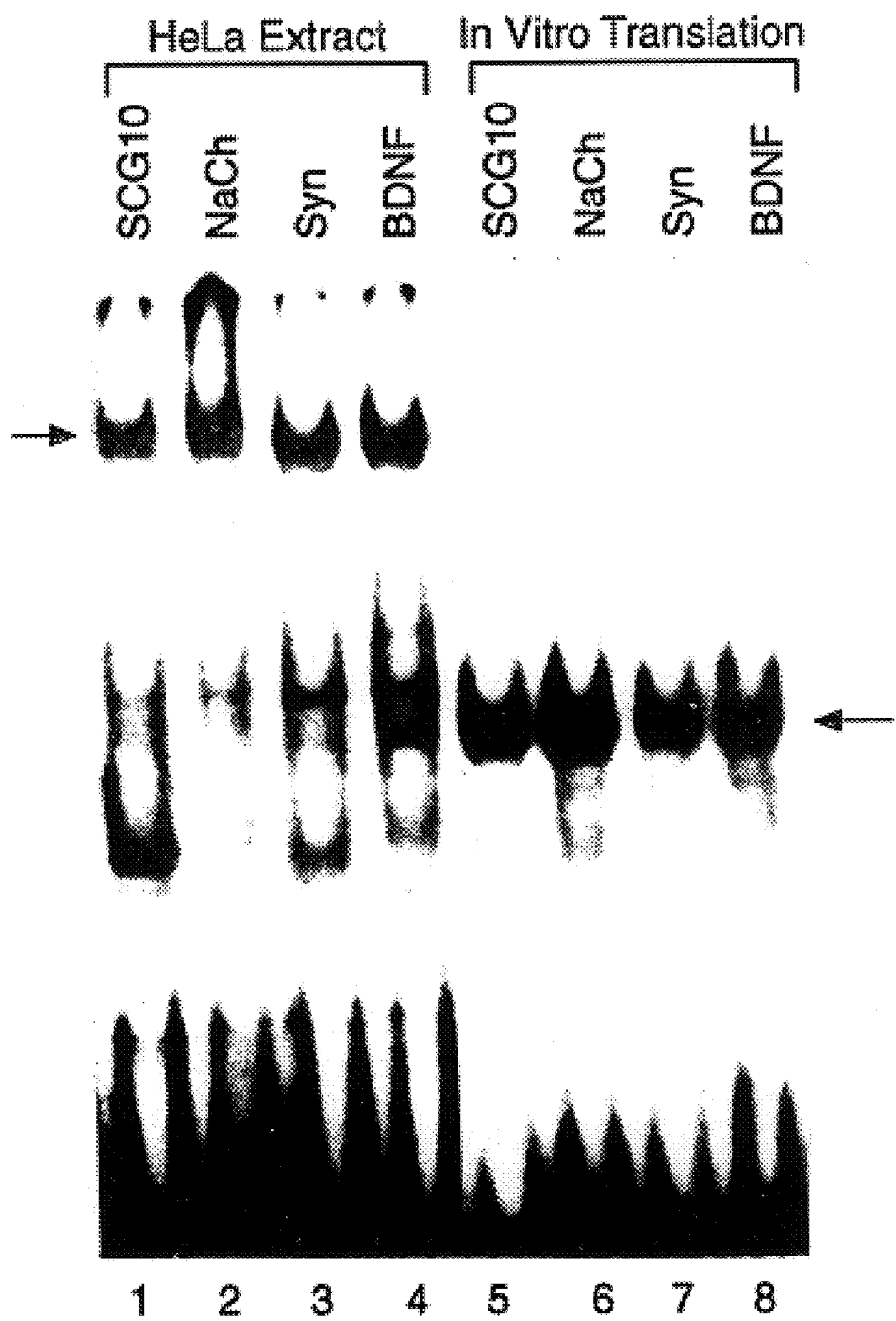
FIG._5

```
GAATTCC GGG GCC CCA GAC CCT GGC GGC GGC TGC GGC AGC CGA GAC GGC      49
        Gly Ala Pro Asp Pro Gly Gly Gly Cys Gly Ser Arg Asp Gly
         1              5                    10

AGG GCG AGG CCC GGA GGC CTG AGC ACC CTC TGC AGC CCC ACT CCT GGG      97
Arg Ala Arg Pro Gly Gly Leu Ser Thr Leu Cys Ser Pro Thr Pro Gly
 15              20                  25                      30

CCT TCT TGG TCC ACG ACG GCC CCA GCA CCC AAC TTT ACC ACC CTC CCC     145
Pro Ser Trp Ser Thr Thr Ala Pro Ala Pro Asn Phe Thr Thr Leu Pro
                 35                  40                      45

CAC CTC TCC CCC GAA ACT CCA GCA ACA AAG AAA AGT AGT CGG AGA AGG     193
His Leu Ser Pro Glu Thr Pro Ala Thr Lys Lys Ser Ser Arg Arg Arg
             50                  55                  60

AGC GGC GAC TCA GGG TCG CCC GCC CCT CCT CAC CGA GGA AGG CCG AAT     241
Ser Gly Asp Ser Gly Ser Pro Ala Pro Pro His Arg Gly Arg Pro Asn
         65                  70                  75

ACA GTT ATG GCC ACC CAG GTA ATG GGG CAG TCT TCT GGA GGA GGA GGG     289
Thr Val Met Ala Thr Gln Val Met Gly Gln Ser Ser Gly Gly Gly Gly
     80                  85                  90

CTG TTT ACC AGC AGT GGC AAC ATT GGA ATG GCC CTG CCT AAC GAC ATG     337
Leu Phe Thr Ser Ser Gly Asn Ile Gly Met Ala Leu Pro Asn Asp Met
 95                 100                 105                 110

TAT GAC TTG CAT GAC CTT TCC AAA GCT GAA CTG GCC GCA CCT CAG CTT     385
Tyr Asp Leu His Asp Leu Ser Lys Ala Glu Leu Ala Ala Pro Gln Leu
                 115                 120                 125

ATT ATG CTG GCA AAT GTG GCC TTA ACT GGG GAA GTA AAT GGC AGC TGC     433
Ile Met Leu Ala Asn Val Ala Leu Thr Gly Glu Val Asn Gly Ser Cys
         130                 135                 140

TGT GAT TAC CTG GTC GGT GAA GAA AGA CAG ATG GCA GAA CTG ATG CCG     481
Cys Asp Tyr Leu Val Gly Glu Glu Arg Gln Met Ala Glu Leu Met Pro
         145                 150                 155

GTT GGG GAT AAC AAC TTT TCA GAT AGT GAA GAA GGA GAA GGA CTT GAA     529
Val Gly Asp Asn Asn Phe Ser Asp Ser Glu Glu Gly Glu Gly Leu Glu
         160                 165                 170

GAG TCT GCT GAT ATA AAA GGT GAA CCT CAT GGA CTG GAA AAC ATG GAA     577
Glu Ser Ala Asp Ile Lys Gly Glu Pro His Gly Leu Glu Asn Met Glu
175             180                 185                     190

CTG AGA AGT TTG GAA CTC AGC GTC GTA GAA CCT CAG CCT GTA TTT GAG     625
Leu Arg Ser Leu Glu Leu Ser Val Val Glu Pro Gln Pro Val Phe Glu
                 195                 200                 205

GCA TCA GGT GCT CCA GAT ATT TAC AGT TCA AAT AAA GAT CTT CCC CCT     673
Ala Ser Gly Ala Pro Asp Ile Tyr Ser Ser Asn Lys Asp Leu Pro Pro
                 210                 215                 220

GAA ACA CCT GGA GCG GAG GAC AAA GGC AAG AGC TCG AAG ACC AAA CCC     721
Glu Thr Pro Gly Ala Glu Asp Lys Gly Lys Ser Ser Lys Thr Lys Pro
             225                 230                 235
```

FIG._6A

```
TTT CGC TGT AAG CCA TGC CAA TAT GAA GCA GAA TCT GAA GAA CAG TTT  769
Phe Arg Cys Lys Pro Cys Gln Tyr Glu Ala Glu Ser Glu Glu Gln Phe
    240             245                 250

GTG CAT CAC ATC AGA GTT CAC AGT GCT AAG AAA TTT TTT GTG GAA GAG  817
Val His His Ile Arg Val His Ser Ala Lys Lys Phe Phe Val Glu Glu
255                 260                 265                 270

AGT GCA GAG AAG CAG GCA AAA GCC AGG GAA TCT GGC TCT TCC ACT GCA  865
Ser Ala Glu Lys Gln Ala Lys Ala Arg Glu Ser Gly Ser Ser Thr Ala
                275                 280                 285

GAA GAG GGA GAT TTC TCC AAG GGC CCC ATT CGC TGT GAC CGC TGC GGC  913
Glu Glu Gly Asp Phe Ser Lys Gly Pro Ile Arg Cys Asp Arg Cys Gly
            290                 295                 300

TAC AAT ACT AAT CGA TAT GAT CAC TAT ACA GCA CAC CTG AAA CAC CAC  961
Tyr Asn Thr Asn Arg Tyr Asp His Tyr Thr Ala His Leu Lys His His
        305                 310                 315

ACC AGA GCT GGG GAT AAT GAG CGA GTC TAC AAG TGT ATC ATT TGC ACA 1009
Thr Arg Ala Gly Asp Asn Glu Arg Val Tyr Lys Cys Ile Ile Cys Thr
    320                 325                 330

TAC ACA ACA GTG AGC GAG TAT CAC TGG AGG AAA CAT TTA AGA AAC CAT 1057
Tyr Thr Thr Val Ser Glu Tyr His Trp Arg Lys His Leu Arg Asn His
335                 340                 345                 350

TTT CCA AGG AAA GTA TAC ACA TGT GGA AAA TGC AAC TAT TTT TCA GAC 1105
Phe Pro Arg Lys Val Tyr Thr Cys Gly Lys Cys Asn Tyr Phe Ser Asp
                355                 360                 365

AGA AAA AAC AAT TAT GTT CAG CAT GTT AGA ACT CAT ACA GGA GAA CGC 1153
Arg Lys Asn Asn Tyr Val Gln His Val Arg Thr His Thr Gly Glu Arg
            370                 375                 380

CCA TAT AAA TGT GAA CTT TGT CCT TAC TCA AGT CTT CAG AAG ACT CAT 1201
Pro Tyr Lys Cys Glu Leu Cys Pro Tyr Ser Ser Ser Gln Lys Thr His
        385                 390                 395

CTA ACT AGA CAT ATG CGT ACT CAT TCA GGT GAG AAG CCA TTT AAA TGT 1249
Leu Thr Arg His Met Arg Thr His Ser Gly Glu Lys Pro Phe Lys Cys
    400                 405                 410

GAT CAG TGC AGT TAT GTG GCC TCT AAT CAA CAT GAA GTA ACC CGC CAT 1297
Asp Gln Cys Ser Tyr Val Ala Ser Asn Gln His Glu Val Thr Arg His
415                 420                 425                 430

GCA AGA CAG GTT CAC AAT GGG CCT AAA CCT CTT AAT TGC CCA CAC TGT 1345
Ala Arg Gln Val His Asn Gly Pro Lys Pro Leu Asn Cys Pro His Cys
                435                 440                 445

GAT TAC AAA ACA GCA GAT AGA AGC AAC TTC AAA AAA CAT GTA GAG CTA 1393
Asp Tyr Lys Thr Ala Asp Arg Ser Asn Phe Lys Lys His Val Glu Leu
            450                 455                 460
```

FIG._6B

```
CAT GTG AAC CCA CGG CAG TTC AAT TGC CCT GTA TGT GAC TAT GCA GCT   1441
His Val Asn Pro Arg Gln Phe Asn Cys Pro Val Cys Asp Tyr Ala Ala
    465                     470                 475

TCC AAG AAG TGT AAT CTA CAG TAT CAC TTC AAA TCT AAG CAT CCT ACT   1489
Ser Lys Lys Cys Asn Leu Gln Tyr His Phe Lys Ser Lys His Pro Thr
    480                     485                 490

TGT CCT AAT AAA ACA ATG GAT GTC TCA AAA GTG AAA CTA AAG AAA ACC   1537
Cys Pro Asn Lys Thr Met Asp Val Ser Lys Val Lys Leu Lys Lys Thr
495             500                 505                 510

AAA AAA CGA GAG GCT GAC TTG CCT GAT AAT ATT ACC AAT GAA AAA ACA   1585
Lys Lys Arg Glu Ala Asp Leu Pro Asp Asn Ile Thr Asn Glu Lys Thr
                515                 520                 525

GAA ATA GAA CAA ACA AAA ATA AAA GGG GAT GTG GCT GGA AAG AAA AAT   1633
Glu Ile Glu Gln Thr Lys Ile Lys Gly Asp Val Ala Gly Lys Lys Asn
                530                 535                 540

GAA AAG TCC GTC AAA GCA GAG AAA AGA GAT GTC TCA AAA GAG AAA AAG   1681
Glu Lys Ser Val Lys Ala Glu Lys Arg Asp Val Ser Lys Glu Lys Lys
            545                 550                 555

CCT TCT AAT AAT GTG TCA GTG ATC CAG GTG ACT ACC AGA ACT CGA AAA   1729
Pro Ser Asn Asn Val Ser Val Ile Gln Val Thr Thr Arg Thr Arg Lys
            560                 565                 570

TCA GTA ACA GAG GTG AAA GAG ATG GAT GTG CAT ACA GGA AGC AAT TCA   1777
Ser Val Thr Glu Val Lys Glu Met Asp Val His Thr Gly Ser Asn Ser
575             580                 585                 590

GAA AAA TTC AGT AAA ACT AAG AAA AGC AAA AGG AAG CTG GAA GTT GAC   1825
Glu Lys Phe Ser Lys Thr Lys Lys Ser Lys Arg Lys Leu Glu Val Asp
                595                 600                 605

AGC CAT TCT TTA CAT GGT CCT GTG AAT GAT GAG GAA TCT TCA ACA AAA   1873
Ser His Ser Leu His Gly Pro Val Asn Asp Glu Glu Ser Ser Thr Lys
                610                 615                 620

AAG AAA AAG AAG GTA GAA AGC AAA TCC AAA AAT AAT AGT CAG GAA GTG   1921
Lys Lys Lys Lys Val Glu Ser Lys Ser Lys Asn Asn Ser Gln Glu Val
                625                 630                 635

CCA AAG GGT GAC AGC AAA GTG GAG GAG AAT AAA AAG CAA AAT ACT TGC   1969
Pro Lys Gly Asp Ser Lys Val Glu Glu Asn Lys Lys Gln Asn Thr Cys
    640                 645                 650

ATG AAA AAA AGT ACA AAG AAG AAA ACT CTG AAA AAT AAA TCA AGT AAG   2017
Met Lys Lys Ser Thr Lys Lys Lys Thr Leu Lys Asn Lys Ser Ser Lys
655             660                 665                 670

AAA AGC AGT AAG CCT TCT CGGAATTC                                  2043
Lys Ser Ser Lys Pro Ser
                675
```

FIG._6C

FIG._7A
FIG._7B

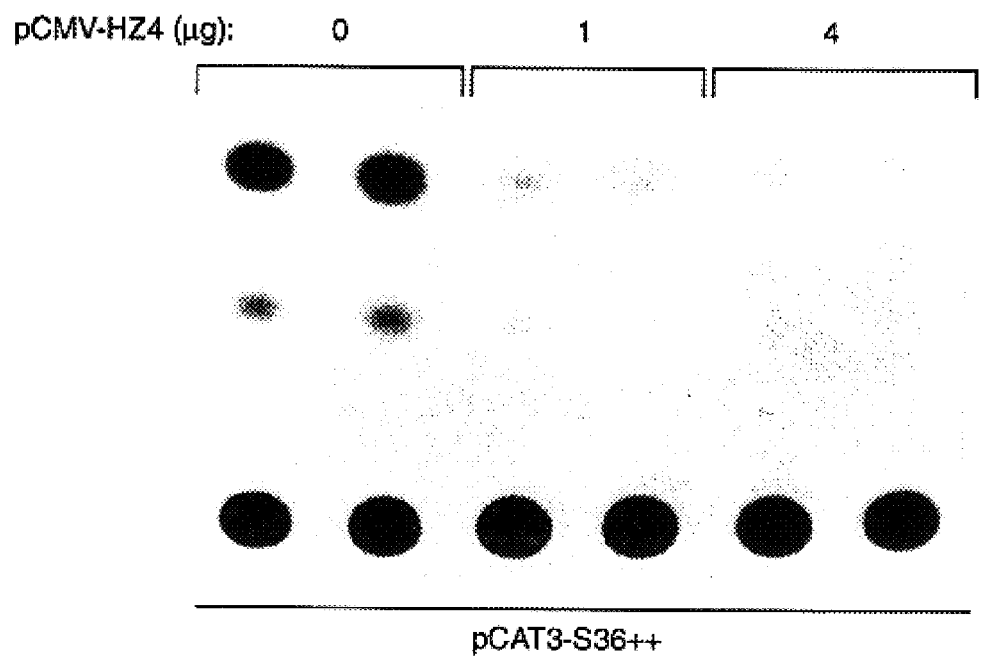
FIG._8A
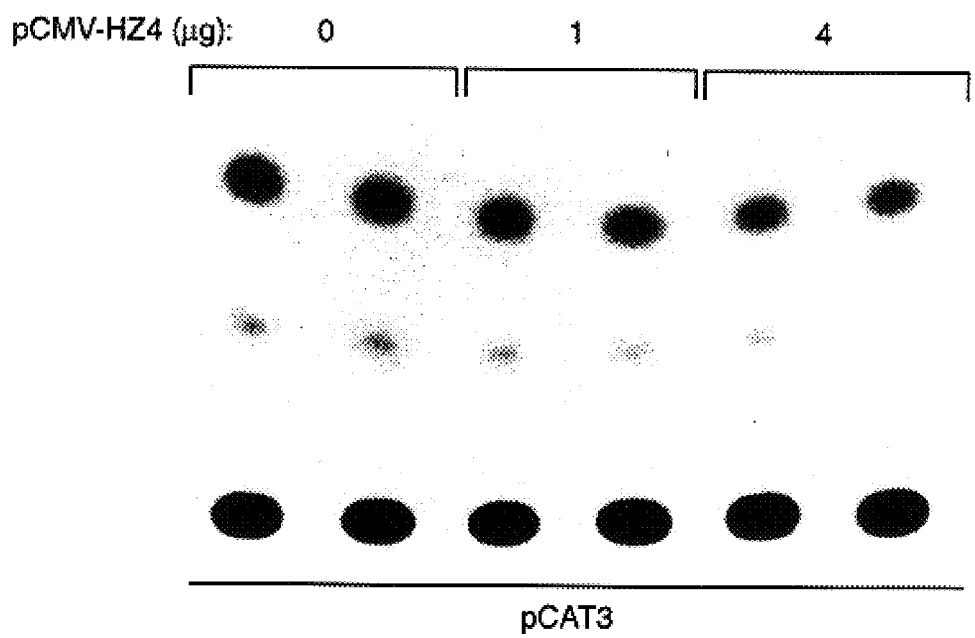
FIG._8B

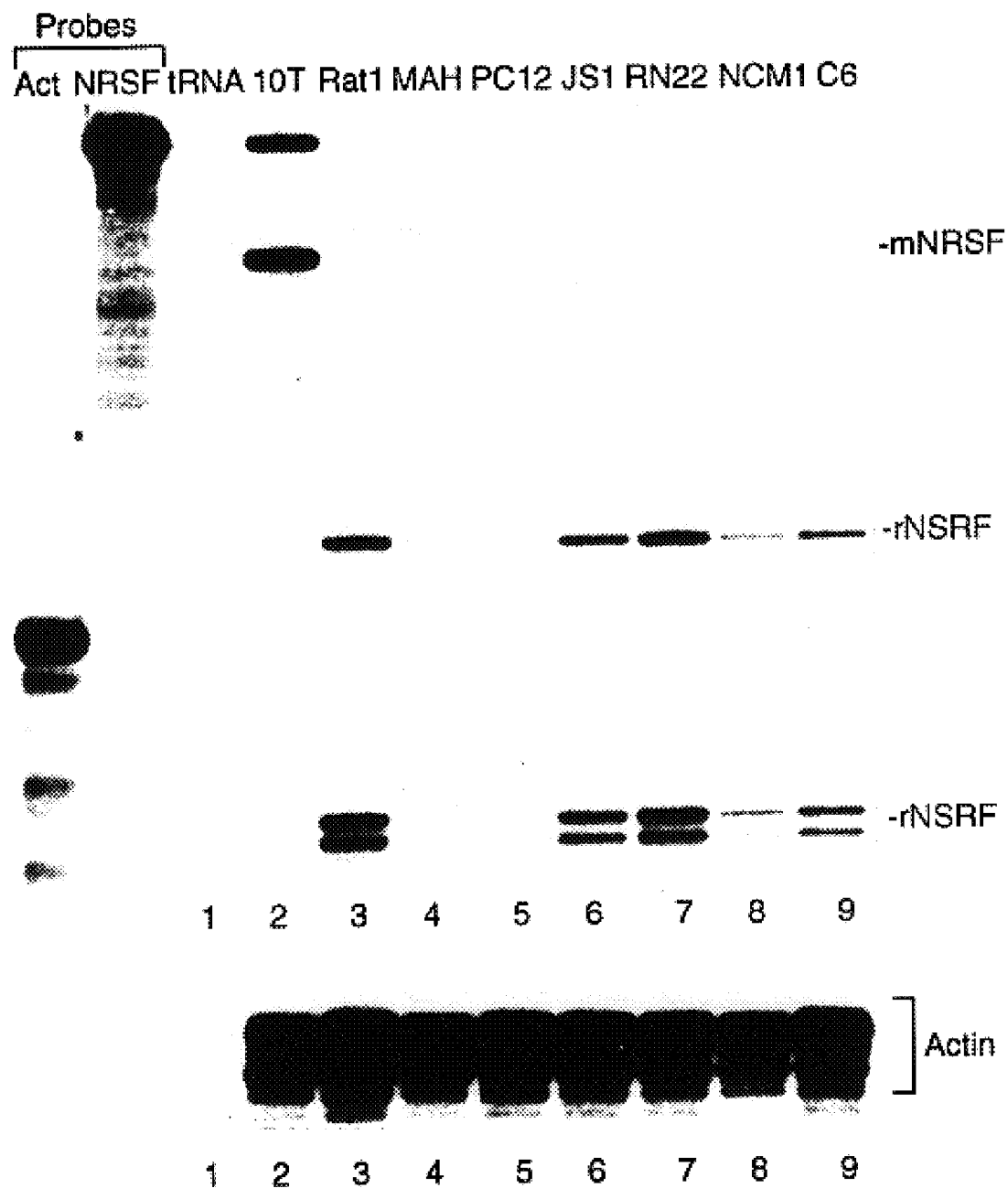
FIG._9

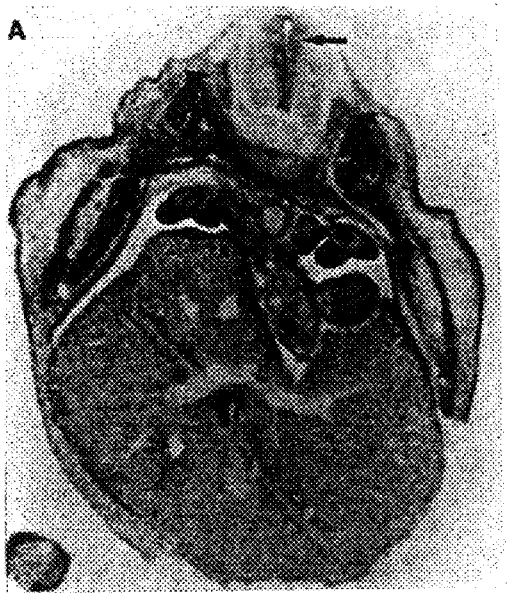
FIG._10A
FIG._10B

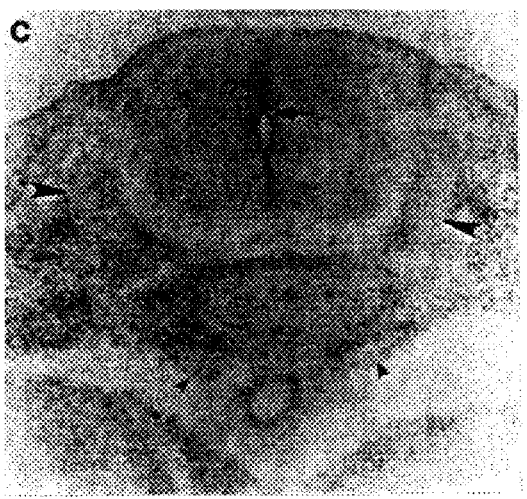 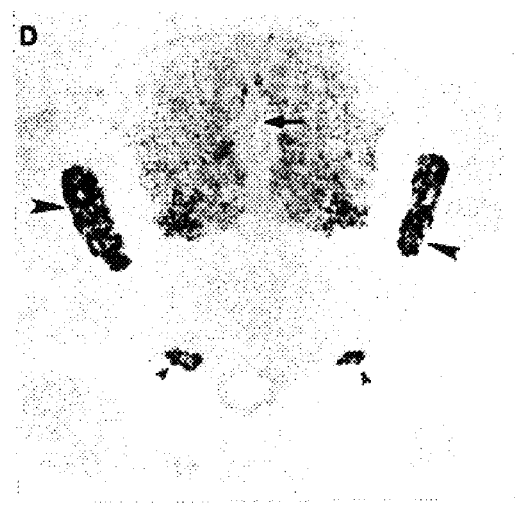
FIG._10C  FIG._10D

  
FIG._11A  FIG._11B  FIG._11C

```
TTCGGACGAG GCGGGCGGGC GGCGACGGCG CGGGCGGGTG CGCGGCGCAG CGTCCTGTGC    60

TGGAATGTGC GGCTCCCGCG AGCTCGCGGC GCAGCAGCAG AAGACCGAGG AGCGCCGCCG   120

AGGCCGCGGG CCCCAGACCC GGGCGGCCGG GACCGCAGCG ACGGCAGAAC CAGGGCCGGC   180

GGTCTGATCC CGCTCCGCGA TCGCACCCCG GGATCTCGAG GGCCTCGACG CCCAACTTTT   240

CCCCGCTCTC CCTCCCCTCC CCTCCCCCGA AAGTCCAGCA ACAAAGAAAA GGAGTTGGAG   300

CGGCGRCGAC GCGGGGGTGG CGGACCGTGG GCGCACAGTT CAGAGGAGTA CAGTT ATG    358
                                                              Met
                                                              1
```

| | | | | | | | | | | | | | | | | |
|---|---|---|---|---|---|---|---|---|---|---|---|---|---|---|---|---|
| GCC | ACC | CAG | GTG | ATG | GGG | CAG | TCT | TCT | GGA | GGA | GGC | AGT | CTC | TTC | AAC | 406 |
| Ala | Thr | Gln | Val | Met | Gly | Gln | Ser | Ser | Gly | Gly | Gly | Ser | Leu | Phe | Asn | |
| | | | 5 | | | | | 10 | | | | | 15 | | | |
| AAC | AGT | GCC | AAC | ATG | GGC | ATG | GSC | TTA | ACC | AAC | GAC | ATG | TAC | GAC | CTG | 454 |
| Asn | Ser | Ala | Asn | Met | Gly | Met | Xaa | Leu | Thr | Asn | Asp | Met | Tyr | Asp | Leu | |
| | | 20 | | | | | 25 | | | | | 30 | | | | |
| CAC | GAG | CTC | TCG | AAA | GCT | GAA | CTG | GCA | GCC | CCT | CAG | CTC | ATC | ATG | TTA | 502 |
| His | Glu | Leu | Ser | Lys | Ala | Glu | Leu | Ala | Ala | Pro | Gln | Leu | Ile | Met | Leu | |
| | 35 | | | | | 40 | | | | | 45 | | | | | |
| GCC | AAC | GTG | GCC | CTG | ACG | GGG | GAG | GCA | AGC | GGC | AGC | TGC | TGC | GAT | TAC | 550 |
| Ala | Asn | Val | Ala | Leu | Thr | Gly | Glu | Ala | Ser | Gly | Ser | Cys | Cys | Asp | Tyr | |
| 50 | | | | | 55 | | | | | 60 | | | | | 65 | |
| CTG | GTC | GGT | GAA | GAG | AGG | CAG | ATG | GCC | GAA | TTG | ATG | CCC | GTG | GGA | GAC | 598 |
| Leu | Val | Gly | Glu | Glu | Arg | Gln | Met | Ala | Glu | Leu | Met | Pro | Val | Gly | Asp | |
| | | | | 70 | | | | | 75 | | | | | 80 | | |
| AAC | CAC | TTC | TCA | GAA | AGT | GAA | GGA | GAA | GGC | CTG | GAA | GAG | TCG | GCT | GAC | 646 |
| Asn | His | Phe | Ser | Glu | Ser | Glu | Gly | Glu | Gly | Leu | Glu | Glu | Ser | Ala | Asp | |
| | | | 85 | | | | | 90 | | | | | 95 | | | |
| CTC | AAA | GGG | CTG | GAA | AAC | ATG | GAA | CTG | GGA | AGT | TTG | GAG | CTA | AGT | GCT | 694 |
| Leu | Lys | Gly | Leu | Glu | Asn | Met | Glu | Leu | Gly | Ser | Leu | Glu | Leu | Ser | Ala | |
| | | 100 | | | | | 105 | | | | | 110 | | | | |
| GTA | GAA | CCC | CAG | CCC | GTA | TTT | GAA | GCC | TCA | GCT | GCC | CCA | GAA | ATA | TAC | 742 |
| Val | Glu | Pro | Gln | Pro | Val | Phe | Glu | Ala | Ser | Ala | Ala | Pro | Glu | Ile | Tyr | |
| | 115 | | | | | 120 | | | | | 125 | | | | | |
| AGC | GCC | AAT | AAA | GAT | CCC | GCT | CCA | GAA | ACA | CCC | GTG | GCG | GAA | GAC | AAA | 790 |
| Ser | Ala | Asn | Lys | Asp | Pro | Ala | Pro | Glu | Thr | Pro | Val | Ala | Glu | Asp | Lys | |
| 130 | | | | 135 | | | | | 140 | | | | | 145 | | |
| TGC | AGG | AGT | TCT | AAG | GCC | AAG | CCC | TTC | CGG | TGT | AAG | CCT | TGC | CAG | TAC | 838 |
| Cys | Arg | Ser | Ser | Lys | Ala | Lys | Pro | Phe | Arg | Cys | Lys | Pro | Cys | Gln | Tyr | |
| | | | 150 | | | | | 155 | | | | | | 160 | | |

FIG._12A

```
GAA GCC GAA TCT GAA GAG CAG TTT GTG CAT CAC ATC CGG ATT CAC AGC    886
Glu Ala Glu Ser Glu Glu Gln Phe Val His His Ile Arg Ile His Ser
            165             170             175

GCT AAG AAG TTC TTT GTG GAG GAA AGT GCA GAG AAA CAG GCC AAA GCC    934
Ala Lys Lys Phe Phe Val Glu Glu Ser Ala Glu Lys Gln Ala Lys Ala
        180             185             190

TGG GAG TCG GGG TCG TCT CCG GCC GAA GAG GGC GAG TTC TCC AAA GGC    982
Trp Glu Ser Gly Ser Ser Pro Ala Glu Glu Gly Glu Phe Ser Lys Gly
        195             200             205

CCC ATC CGC TGT GAC CGC TGT GGC TAC AAT ACC AAC CGG TAT GAC CAC    1030
Pro Ile Arg Cys Asp Arg Cys Gly Tyr Asn Thr Asn Arg Tyr Asp His
210             215             220             225

TAC ATG GCA CAC CTG AAG CAC CAC CTG CGA GCT GGC GAG AAC GAG CGC    1078
Tyr Met Ala His Leu Lys His His Leu Arg Ala Gly Glu Asn Glu Arg
            230             235             240

ATC TAC AAG TGC ATC ATC TGC ACG TAC ACG ACG GTC AGC GAG TAC CAC    1126
Ile Tyr Lys Cys Ile Ile Cys Thr Tyr Thr Thr Val Ser Glu Tyr His
            245             250             255

TGG AGG AAA CAC CTG AGA AAC CAT TTC CCC AGG AAA GTC TAC ACC TGC    1174
Trp Arg Lys His Leu Arg Asn His Phe Pro Arg Lys Val Tyr Thr Cys
        260             265             270

AGC AAG TGC AAC TAC TTC TCA GAC AGA AAA AAT AAC TAC GTT CAG CAC    1222
Ser Lys Cys Asn Tyr Phe Ser Asp Arg Lys Asn Asn Tyr Val Gln His
    275             280             285

GTG CGA ACT CAC ACA GGA GAA CGC CCG TAT AAA TGT GAA CTT TGT CCT    1270
Val Arg Thr His Thr Gly Glu Arg Pro Tyr Lys Cys Glu Leu Cys Pro
290             295             300             305

TAC TCA AGC TCT CAG AAG ACT CAT CTA ACG CGA CAC ATG CGG ACT CAT    1318
Tyr Ser Ser Ser Gln Lys Thr His Leu Thr Arg His Met Arg Thr His
            310             315             320

TCA GGT GAG AAG CCA TTT AAA TGT GAT GAG TGC AAT TAT GTG GCC TCT    1366
Ser Gly Glu Lys Pro Phe Lys Cys Asp Glu Cys Asn Tyr Val Ala Ser
            325             330             335

AAT CAG CAT GAA GTG ACC CGA CAT GCA AGA CAG GTT CAC AAC GGG CCT    1414
Asn Gln His Glu Val Thr Arg His Ala Arg Gln Val His Asn Gly Pro
        340             345             350

AAA CCT CTT AAT TGC CCG CAC TGT GAC TAC AAA ACA GCA GAT AGA AGC    1462
Lys Pro Leu Asn Cys Pro His Cys Asp Tyr Lys Thr Ala Asp Arg Ser
    355             360             365

AAC TTC AAA AAG CAC GTG GAG CTG CAT GTT AAC CCA CGG CAG TTC AAC    1510
Asn Phe Lys Lys His Val Glu Leu His Val Asn Pro Arg Gln Phe Asn
370             375             380             385
```

FIG._12B

```
TGC CCC GTG TGT GAC TAC GCG GCT TCT AAG AAG TGT AAT CTA CAA TAC         1558
Cys Pro Val Cys Asp Tyr Ala Ala Ser Lys Lys Cys Asn Leu Gln Tyr
        390             395             400

CAT TTC AAA TCT AAG CAT CCC ACC TGT CCC AGC AAA ACA ATG GAT GTC         1606
His Phe Lys Ser Lys His Pro Thr Cys Pro Ser Lys Thr Met Asp Val
        405             410             415

TCC AAA GTG AAG CTA AAG AAA ACC AAA AAG AGA GAG GCT GAC CTG CTT         1654
Ser Lys Val Lys Leu Lys Lys Thr Lys Lys Arg Glu Ala Asp Leu Leu
        420             425             430

AAT AAC GCC GTC AGC AAC GAG AAG ATG GAG AAT GAG CAA ACA AAA ACA         1702
Asn Asn Ala Val Ser Asn Glu Lys Met Glu Asn Glu Gln Thr Lys Thr
        435             440             445

AAG GGG GAT GTG TCT GGG AAG AAG AAC GAG AAA CCT GTA AAA GCT GTG         1750
Lys Gly Asp Val Ser Gly Lys Lys Asn Glu Lys Pro Val Lys Ala Val
450             455             460             465

GGA AAA GAT GCT TCA AAA GAG AAG AAG CCT GGT AGC AGT GTC TCA GTG         1798
Gly Lys Asp Ala Ser Lys Glu Lys Lys Pro Gly Ser Ser Val Ser Val
            470             475             480

GTC CAG GTA ACT ACC AGG ACT CGG AAG TCA GCG GTG GCG GCG GAG ACT         1846
Val Gln Val Thr Thr Arg Thr Arg Lys Ser Ala Val Ala Ala Glu Thr
            485             490             495

AAA GCA GCA GAG GTG AAA CAC ACA GAC GGA CAA ACA GGA AAC AAT CCA         1894
Lys Ala Ala Glu Val Lys His Thr Asp Gly Gln Thr Gly Asn Asn Pro
        500             505             510

GAA AAG CCC TGT AAA GCC AAG AAA AAC AAA AGA AAG AAG GAT GCT GAG         1942
Glu Lys Pro Cys Lys Ala Lys Lys Asn Lys Arg Lys Lys Asp Ala Glu
        515             520             525

GCC CAT CCC TCC GAC GAG CCT GTG AAC GAG GGA CCA GTG ACA AAA AAG         1990
Ala His Pro Ser Asp Glu Pro Val Asn Glu Gly Pro Val Thr Lys Lys
530             535             540             545

AAA AAG AAG TCT GAG TGC AAA TCA AAA ATC AGT ACC AAC GTG CCA AAG         2038
Lys Lys Lys Ser Glu Cys Lys Ser Lys Ile Ser Thr Asn Val Pro Lys
            550             555             560

GGC GGC GGC CGA GCG GAG GAG AGG CCG GGG GTC AAG AAG CAA AGC GCT         2086
Gly Gly Gly Arg Ala Glu Glu Arg Pro Gly Val Lys Lys Gln Ser Ala
            565             570             575

TCC CTT AAG AAA GGC ACA AAG AAG ACG CCG CCC AAG ACA AAG ACA AGT         2134
Ser Leu Lys Lys Gly Thr Lys Lys Thr Pro Pro Lys Thr Lys Thr Ser
        580             585             590

AAA AAA GGT GGC AAA CTT GCT CCC ACG GAG CCT GCC CCT CCC ACG GGG         2182
Lys Lys Gly Gly Lys Leu Ala Pro Thr Glu Pro Ala Pro Pro Thr Gly
        595             600             605
```

FIG.—12C

```
CTT GCC GAG ATG GAA CCT TCT CCC ACG GAG CCT TCC CAG AAG GAA CCA      2230
Leu Ala Glu Met Glu Pro Ser Pro Thr Glu Pro Ser Gln Lys Glu Pro
610                 615                 620                 625

CCT CCC AGT ATG GAG CCT CCC TGC CCC GAG GAG CTG CCT CAG GCC GAG      2278
Pro Pro Ser Met Glu Pro Pro Cys Pro Glu Glu Leu Pro Gln Ala Glu
                630                 635                 640

CCA CCT CCT ATG GAG GAT TGT CAG AAG GAG CTG CCT TCT CCC GTG GAG      2326
Pro Pro Pro Met Glu Asp Cys Gln Lys Glu Leu Pro Ser Pro Val Glu
            645                 650                 655

CCC GCT CAG ATT GAG GTT GCT CAG ACG GCC CCT ACG CAG GTT CAG GAG      2374
Pro Ala Gln Ile Glu Val Ala Gln Thr Ala Pro Thr Gln Val Gln Glu
        660                 665                 670

GAG CCC CCT CCT GTC TCG GAG CCA CCT CGG GTG AAG CCA ACC AAA AGA      2422
Glu Pro Pro Pro Val Ser Glu Pro Pro Arg Val Lys Pro Thr Lys Arg
    675                 680                 685

TCA TCT CTC CGG AAA GAC AGA GCA GAG AAG GAG CTG AGC CTG CTG AGT      2470
Ser Ser Leu Arg Lys Asp Arg Ala Glu Lys Glu Leu Ser Leu Leu Ser
690                 695                 700                 705

GAG ATG GCG CGG CAG GAG CAG GTC CTC ATG GGG GTT GGC TTG GTG CCT      2518
Glu Met Ala Arg Gln Glu Gln Val Leu Met Gly Val Gly Leu Val Pro
                710                 715                 720

GTT AGA GAC AGC AAG CTT CTG AAG GGA AAC AAG AGC GCC CAG GAC CCC      2566
Val Arg Asp Ser Lys Leu Leu Lys Gly Asn Lys Ser Ala Gln Asp Pro
            725                 730                 735

CCA GCC CCA CCG TCA CCA TCG CCA AAG GGA AAC TCG AGG GAA GAG ACA      2614
Pro Ala Pro Pro Ser Pro Ser Pro Lys Gly Asn Ser Arg Glu Glu Thr
        740                 745                 750

CCC AAG GAC CAA GAA ATG GTC TCT GAT GGG GAA GGA ACT ATA GTA TTC      2662
Pro Lys Asp Gln Glu Met Val Ser Asp Gly Glu Gly Thr Ile Val Phe
    755                 760                 765

CCT CTC AAG AAA GGA GGA CCA GAG GAA GCT GGA GAG AGT CCA GCT GAG      2710
Pro Leu Lys Lys Gly Gly Pro Glu Glu Ala Gly Glu Ser Pro Ala Glu
770                 775                 780                 785

TTG GCT GCT CTC AAG GAG TCT GCC CGT GTT TCA TCC TCT GAA CAA AAC      2758
Leu Ala Ala Leu Lys Glu Ser Ala Arg Val Ser Ser Ser Glu Gln Asn
                790                 795                 800

TCA GCC ATG CCA GAG GGT GGA GCA TCA CAC AGC AAG TGT CAG ACT GGC      2806
Ser Ala Met Pro Glu Gly Gly Ala Ser His Ser Lys Cys Gln Thr Gly
            805                 810                 815

TCC TCT GGG CTT TGT GAC GTG GAC ACT GAG CAG AAG ACA GAT ACT GTC      2854
Ser Ser Gly Leu Cys Asp Val Asp Thr Glu Gln Lys Thr Asp Thr Val
        820                 825                 830
```

FIG._12D

```
CCC ATG AAA GAC TCC GCA GCA GAG CCA GTG TCC CCT CCT ACC CCA ACA    2902
Pro Met Lys Asp Ser Ala Ala Glu Pro Val Ser Pro Pro Thr Pro Thr
    835             840                 845

GTG GAC CGT GAC GCA GGG TCA CCA GCT GTA GTG GCC TCC CCT CCT ATC    2950
Val Asp Arg Asp Ala Gly Ser Pro Ala Val Val Ala Ser Pro Pro Ile
850             855                 860                 865

ACG TTG GCT GAA AAC GAG TCT CAG GAA ATT GAT GAA GAT GAA GGC ATC    2998
Thr Leu Ala Glu Asn Glu Ser Gln Glu Ile Asp Glu Asp Glu Gly Ile
                870                 875                 880

CAT AGC CAT GAT GGA AGT GAC CTG AGT GAC AAC ATG TCT GAG GGG AGT    3046
His Ser His Asp Gly Ser Asp Leu Ser Asp Asn Met Ser Glu Gly Ser
            885                 890                 895

GAC GAC TCA GGA CTG CAC GGG GCT CGG CCG ACA CCA CCA GAA GCT ACG    3094
Asp Asp Ser Gly Leu His Gly Ala Arg Pro Thr Pro Pro Glu Ala Thr
        900                 905                 910

TCA AAA AAT GGG AAG GCA GGG TTG GCT GGT AAA GTG ACT GAG GGA GAG    3142
Ser Lys Asn Gly Lys Ala Gly Leu Ala Gly Lys Val Thr Glu Gly Glu
    915                 920                 925

TTT GTG TGT ATT TTC TGT GAT CGT TCT TTT AGA AAG GAA AAA GAT TAT    3190
Phe Val Cys Ile Phe Cys Asp Arg Ser Phe Arg Lys Glu Lys Asp Tyr
930             935                 940                 945

AGC AAA CAC CTC AAT CGC CAC TTG GTG AAT GTG TAC TTC CTA GAA GAA    3238
Ser Lys His Leu Asn Arg His Leu Val Asn Val Tyr Phe Leu Glu Glu
                950                 955                 960

GCA GCT GAG GAG CAG GAG GAG CAG GAG GAG CGG GAG GAG CAG GAG TAG    3286
Ala Ala Glu Glu Gln Glu Glu Gln Glu Glu Arg Glu Glu Gln Glu  *
            965                 970                 975

CTGAGCCTCG GGAGAAGCAC CGTGCAGACT TTGTGAGCAT GCAATTTTAA TTTGTAGACA    3346
AACGCAAGCT TGCTTTAATT AGTCTCCAAG GCTGAGTTTT CAGTAACATT CTTTTTCTTA    3406
GGACTGTACA TCTATTTAGT GTTTGTTGCA TAAATCTTAG CAAATCCTCG GGAGTTAATG    3466
TAAGAGGACA GATATGTAAC TAGCTCGTGC AGGCAGGTGC AAGGAGAAGG GTAAGATGGT    3526
GGAACACACC ACTTGCCTTG TCTGCCTACA ACCTGTTGGG TTTTCTTTTC ACGGTAGTTC    3586
CTAATTTTTA GTTACTTGTT TAGATCGATA AAAATTGGCT TAGTAAATTA CTTGAAGAAT    3646
TTGCCTGCTT TATATAAATT AAGTTAGCAC TTTACAGTTY CTTTAGAGAT GAAAAAAAAG    3706
AGATTTTAAT TGGAGAGAAA TTCTCAACAT TGGACATTGT ATCTGTCCAG GTAATTGCTT    3766
CCTAACTTGC TATCAATATT TTGTGTTTAT ATGTTAATCG TTATAAAAAG TGATTTTTGT    3826
TTTTTGGGTA TTTTTTATTT TGGTGCTTTT CTGGCTTAAG ATGTTGCACA TGGTTCTTGT    3886
TTTTGTTTCT TTAACCTATG CAGTTAATCT CCCTTCCCCT GAAACAGCGT TGTGTTAAAT    3946
AGTAACACTA TACAGATATA TGCATGGTTT TTTTTTTTGT TTGTTTGTTT GTTTGTTTTT    4006
CCTTTTTGGA GGGATGCTTT TAGGCTTGTT TGCCTCGTSC CGAATTCGAT A             4057
```

FIG._12E

SEQUENCE LISTING

<160> NUMBER OF SEQ ID NOS: 55

<210> SEQ ID NO 1
<211> LENGTH: 31
<212> TYPE: DNA
<213> ORGANISM: Rattus rattus
<220> FEATURE:
<221> NAME/KEY: misc_structure
<222> LOCATION: (1)..(31)
<223> OTHER INFORMATION: Rat SCG10
<220> FEATURE:
<221> NAME/KEY: variation
<222> LOCATION: (15)
<223> OTHER INFORMATION: n = a or g or t/u or c
<220> FEATURE:
<221> NAME/KEY: variation
<222> LOCATION: (23)
<223> OTHER INFORMATION: n = a or g or t/u or c

<400> SEQUENCE: 1
gccatttcag caccncggag agngcctctg c                              31

<210> SEQ ID NO 2
<211> LENGTH: 31
<212> TYPE: DNA
<213> ORGANISM: Rattus rattus
<220> FEATURE:
<221> NAME/KEY: misc_structure
<222> LOCATION: (1)..(31)
<223> OTHER INFORMATION: Rat type II sodium channel
<220> FEATURE:
<221> NAME/KEY: variation
<222> LOCATION: (15)
<223> OTHER INFORMATION: n = a or g or t/u or c
<220> FEATURE:
<221> NAME/KEY: variation
<222> LOCATION: (23)
<223> OTHER INFORMATION: n = a or g or t/u or c

<400> SEQUENCE: 2
tgggtttcag aaccncggac agnaccagag t                              31

<210> SEQ ID NO 3
<211> LENGTH: 31
<212> TYPE: DNA
<213> ORGANISM: Homo sapiens
<220> FEATURE:
<221> NAME/KEY: misc_structure
<222> LOCATION: (1)..(31)
<223> OTHER INFORMATION: Human synapsin I
<220> FEATURE:
<221> NAME/KEY: variation
<222> LOCATION: (15)
<223> OTHER INFORMATION: n = a or g or t/u or c
<220> FEATURE:
<221> NAME/KEY: variation
<222> LOCATION: (23)
<223> OTHER INFORMATION: n = a or g or t/u or c

<400> SEQUENCE: 3
ccagcttcag caccncggag agngccttcg c                              31

<210> SEQ ID NO 4
<211> LENGTH: 31
<212> TYPE: DNA
<213> ORGANISM: Rattus rattus
<220> FEATURE:
<221> NAME/KEY: misc_structure
<222> LOCATION: (1)..(31)
<223> OTHER INFORMATION: Rat brain-derived neurotrophic factor (BDNF)

```
<220> FEATURE:
<221> NAME/KEY: variation
<222> LOCATION: (15)
<223> OTHER INFORMATION: n = a or g or t/u or c
<220> FEATURE:
<221> NAME/KEY: variation
<222> LOCATION: (23)
<223> OTHER INFORMATION: n = a or g or t/u or c

<400> SEQUENCE: 4
gtccattcag caccntggag agngccagcg g                              31

<210> SEQ ID NO 5
<211> LENGTH: 30
<212> TYPE: DNA
<213> ORGANISM: Homo sapiens
<220> FEATURE:
<221> NAME/KEY: misc_structure
<222> LOCATION: (1)..(30)
<223> OTHER INFORMATION: Human glycine receptor subnunit
<220> FEATURE:
<221> NAME/KEY: variation
<222> LOCATION: (15)
<223> OTHER INFORMATION: n = a or g or t/u or c
<220> FEATURE:
<221> NAME/KEY: variation
<222> LOCATION: (23)
<223> OTHER INFORMATION: n = a or g or t/u or c

<400> SEQUENCE: 5
ggcgtttcag caccncggag agngtccaga                                30

<210> SEQ ID NO 6
<211> LENGTH: 31
<212> TYPE: DNA
<213> ORGANISM: Homo sapiens
<220> FEATURE:
<221> NAME/KEY: misc_structure
<222> LOCATION: (1)..(31)
<223> OTHER INFORMATION: Human NMDA receptor subunit (NR1-1)
<220> FEATURE:
<221> NAME/KEY: variation
<222> LOCATION: (15)
<223> OTHER INFORMATION: n = a or g or t/u or c
<220> FEATURE:
<221> NAME/KEY: variation
<222> LOCATION: (23)
<223> OTHER INFORMATION: n = a or g or t/u or c

<400> SEQUENCE: 6
cccgcttcag caccncggag agngccggcc g                              31

<210> SEQ ID NO 7
<211> LENGTH: 31
<212> TYPE: DNA
<213> ORGANISM: Homo sapiens
<220> FEATURE:
<221> NAME/KEY: misc_structure
<222> LOCATION: (1)..(31)
<223> OTHER INFORMATION: Human acetylcholine (ACh) receptor B2 subunit
<220> FEATURE:
<221> NAME/KEY: variation
<222> LOCATION: (15)
<223> OTHER INFORMATION: n = a or g or t/u or c
<220> FEATURE:
<221> NAME/KEY: variation
<222> LOCATION: (23)
<223> OTHER INFORMATION: n = a or g or t/u or c

<400> SEQUENCE: 7
gcggcttcag caccncggag agngccccac c                              31
```

```
<210> SEQ ID NO 8
<211> LENGTH: 31
<212> TYPE: DNA
<213> ORGANISM: Gallus gallus
<220> FEATURE:
<221> NAME/KEY: misc_structure
<222> LOCATION: (1)..(31)
<223> OTHER INFORMATION: Chicken middle molecular weight neurofilament
      (neurofilament M)
<220> FEATURE:
<221> NAME/KEY: variation
<222> LOCATION: (15)
<223> OTHER INFORMATION: n = a or g or t/u/ or c
<220> FEATURE:
<221> NAME/KEY: variation
<222> LOCATION: (23)
<223> OTHER INFORMATION: n = a or g or t/u or c

<400> SEQUENCE: 8
ggggtttcag caccncggag agntcccgcg g                                   31

<210> SEQ ID NO 9
<211> LENGTH: 31
<212> TYPE: DNA
<213> ORGANISM: Gallus gallus
<220> FEATURE:
<221> NAME/KEY: misc_structure
<222> LOCATION: (1)..(31)
<223> OTHER INFORMATION: Chicken neuron-specific B4 tubulin
<220> FEATURE:
<221> NAME/KEY: variation
<222> LOCATION: (15)
<223> OTHER INFORMATION: n = a or g or t/u or c
<220> FEATURE:
<221> NAME/KEY: variation
<222> LOCATION: (23)
<223> OTHER INFORMATION: n = a or g or t/u or c

<400> SEQUENCE: 9
cgccgttcag caccncggag agngccgcct g                                   31

<210> SEQ ID NO 10
<211> LENGTH: 31
<212> TYPE: DNA
<213> ORGANISM: Homo sapiens
<220> FEATURE:
<221> NAME/KEY: misc_structure
<222> LOCATION: (1)..(31)
<223> OTHER INFORMATION: Human cortitrpin releasing factor (CRF)
<220> FEATURE:
<221> NAME/KEY: variation
<222> LOCATION: (15)
<223> OTHER INFORMATION: n = a or g or t/u or c
<220> FEATURE:
<221> NAME/KEY: variation
<222> LOCATION: (23)
<223> OTHER INFORMATION: n = a or g or t/u or c

<400> SEQUENCE: 10
ggcgcttcag caccncggag agngcccatc c                                   31

<210> SEQ ID NO 11
<211> LENGTH: 31
<212> TYPE: DNA
<213> ORGANISM: Gallus gallus
<220> FEATURE:
<221> NAME/KEY: misc_structure
<222> LOCATION: (1)..(31)
<223> OTHER INFORMATION: Chicken calbindin
<220> FEATURE:
<221> NAME/KEY: variation
<222> LOCATION: (15)
```

```
<223> OTHER INFORMATION: n = a or g or t/u or c
<220> FEATURE:
<221> NAME/KEY: variation
<222> LOCATION: (23)
<223> OTHER INFORMATION: n = a or g or t/u or c

<400> SEQUENCE: 11
gcacagtcag caccncggag agngcccccg c                              31

<210> SEQ ID NO 12
<211> LENGTH: 31
<212> TYPE: DNA
<213> ORGANISM: Mus musculus
<220> FEATURE:
<221> NAME/KEY: misc_structure
<222> LOCATION: (1)..(31)
<223> OTHER INFORMATION: Mouse synaptotagmin-4
<220> FEATURE:
<221> NAME/KEY: variation
<222> LOCATION: (15)
<223> OTHER INFORMATION: n = a or g or t/u or c
<220> FEATURE:
<221> NAME/KEY: variation
<222> LOCATION: (23)
<223> OTHER INFORMATION: n = a or g or t/u or c

<400> SEQUENCE: 12
gttctttcag caccncggag agngcacgca g                              31

<210> SEQ ID NO 13
<211> LENGTH: 31
<212> TYPE: DNA
<213> ORGANISM: Rattus rattus
<220> FEATURE:
<221> NAME/KEY: misc_feature
<222> LOCATION: (1)..(31)
<223> OTHER INFORMATION: Rat transcription factor HES-3
<220> FEATURE:
<221> NAME/KEY: variation
<222> LOCATION: (15)
<223> OTHER INFORMATION: n = a or g or t/u or c
<220> FEATURE:
<221> NAME/KEY: variation
<222> LOCATION: (23)
<223> OTHER INFORMATION: n = a or g or t/u or c

<400> SEQUENCE: 13
gggcaggcag caccncggag agngccaacc c                              31

<210> SEQ ID NO 14
<211> LENGTH: 31
<212> TYPE: DNA
<213> ORGANISM: Rattus rattus
<220> FEATURE:
<221> NAME/KEY: misc_structure
<222> LOCATION: (1)..(31)
<223> OTHER INFORMATION: Rat synaptophysin
<220> FEATURE:
<221> NAME/KEY: variation
<222> LOCATION: (15)
<223> OTHER INFORMATION: n = a or g or t/u or c
<220> FEATURE:
<221> NAME/KEY: variation
<222> LOCATION: (23)
<223> OTHER INFORMATION: n = a or g or t/u or c

<400> SEQUENCE: 14
cgcgctccag caccntggag agngcccggc g                              31

<210> SEQ ID NO 15
<211> LENGTH: 21
```

```
<212> TYPE: DNA
<213> ORGANISM: Homo sapiens
<220> FEATURE:
<221> NAME/KEY: misc_structure
<222> LOCATION: (1)..(21)
<223> OTHER INFORMATION: Human calbindin
<220> FEATURE:
<221> NAME/KEY: variation
<222> LOCATION: (10)
<223> OTHER INFORMATION: n = a or g or t/u or c
<220> FEATURE:
<221> NAME/KEY: variation
<222> LOCATION: (18)
<223> OTHER INFORMATION: n = a or g or t/u or c

<400> SEQUENCE: 15
agcagcaccn aggagagngc c                                      21

<210> SEQ ID NO 16
<211> LENGTH: 21
<212> TYPE: DNA
<213> ORGANISM: Gallus gallus
<220> FEATURE:
<221> NAME/KEY: misc_structure
<222> LOCATION: (1)..(21)
<223> OTHER INFORMATION: Chicken calbindin
<220> FEATURE:
<221> NAME/KEY: variation
<222> LOCATION: (10)
<223> OTHER INFORMATION: n = a or g or t/u or c
<220> FEATURE:
<221> NAME/KEY: variation
<222> LOCATION: (18)
<223> OTHER INFORMATION: n = a or g or t/u or c

<400> SEQUENCE: 16
gtcagcaccn cggagagngc c                                      21

<210> SEQ ID NO 17
<211> LENGTH: 21
<212> TYPE: DNA
<213> ORGANISM: Rattus rattus
<220> FEATURE:
<221> NAME/KEY: misc_structure
<222> LOCATION: (1)..(21)
<223> OTHER INFORMATION: Rat calbindin
<220> FEATURE:
<221> NAME/KEY: variation
<222> LOCATION: (10)
<223> OTHER INFORMATION: n = a or g or t/u or c
<220> FEATURE:
<221> NAME/KEY: variation
<222> LOCATION: (18)
<223> OTHER INFORMATION: n = a or g or t/u or c

<400> SEQUENCE: 17
agcagcaccn cggagagngc c                                      21

<210> SEQ ID NO 18
<211> LENGTH: 21
<212> TYPE: DNA
<213> ORGANISM: Mus musculus
<220> FEATURE:
<221> NAME/KEY: misc_structure
<222> LOCATION: (1)..(21)
<223> OTHER INFORMATION: Mouse calbindin
<220> FEATURE:
<221> NAME/KEY: variation
<222> LOCATION: (10)
<223> OTHER INFORMATION: n = a or g or t/u or c
<220> FEATURE:
<221> NAME/KEY: variation
<222> LOCATION: (18)
```

<223> OTHER INFORMATION: n = a or g or t/u or c

<400> SEQUENCE: 18
agcagcaccn cggagagngc c          21

<210> SEQ ID NO 19
<211> LENGTH: 21
<212> TYPE: DNA
<213> ORGANISM: Homo sapiens
<220> FEATURE:
<221> NAME/KEY: misc_structure
<222> LOCATION: (1)..(21)
<223> OTHER INFORMATION: Human CRF
<220> FEATURE:
<221> NAME/KEY: variation
<222> LOCATION: (10)
<223> OTHER INFORMATION: n = a or g or t/u or c
<220> FEATURE:
<221> NAME/KEY: variation
<222> LOCATION: (18)
<223> OTHER INFORMATION: n = a or g or t/u or c

<400> SEQUENCE: 19
ttcagcaccn cggagagngc c          21

<210> SEQ ID NO 20
<211> LENGTH: 21
<212> TYPE: DNA
<213> ORGANISM: Rattus rattus
<220> FEATURE:
<221> NAME/KEY: misc_structure
<222> LOCATION: (1)..(21)
<223> OTHER INFORMATION: Rat CRF
<220> FEATURE:
<221> NAME/KEY: variation
<222> LOCATION: (10)
<223> OTHER INFORMATION: n = a or g or t/u or c
<220> FEATURE:
<221> NAME/KEY: variation
<222> LOCATION: (18)
<223> OTHER INFORMATION: n = a or g or t/u or c

<400> SEQUENCE: 20
ttcagcaccn cggagagngt c          21

<210> SEQ ID NO 21
<211> LENGTH: 21
<212> TYPE: DNA
<213> ORGANISM: Ovis aries
<220> FEATURE:
<221> NAME/KEY: misc_structure
<222> LOCATION: (1)..(21)
<223> OTHER INFORMATION: Sheep CRF
<220> FEATURE:
<221> NAME/KEY: variation
<222> LOCATION: (10)
<223> OTHER INFORMATION: n = a or g or t/u or c
<220> FEATURE:
<221> NAME/KEY: variation
<222> LOCATION: (18)
<223> OTHER INFORMATION: n = a or g or t/u or c

<400> SEQUENCE: 21
ttcagcactn cggagagngc c          21

<210> SEQ ID NO 22
<211> LENGTH: 21
<212> TYPE: DNA
<213> ORGANISM: Xenopus laevis
<220> FEATURE:
<221> NAME/KEY: misc_structure

```
<222> LOCATION: (1)..(21)
<223> OTHER INFORMATION: Xenopus CRF
<220> FEATURE:
<221> NAME/KEY: variation
<222> LOCATION: (10)
<223> OTHER INFORMATION: n = a or g or t/u or c
<220> FEATURE:
<221> NAME/KEY: variation
<222> LOCATION: (18)
<223> OTHER INFORMATION: n = a or g or t/u or c

<400> SEQUENCE: 22
ttcagcaccn cggagagnga a                                      21

<210> SEQ ID NO 23
<211> LENGTH: 21
<212> TYPE: DNA
<213> ORGANISM: Homo sapiens
<220> FEATURE:
<221> NAME/KEY: misc_structure
<222> LOCATION: (1)..(21)
<223> OTHER INFORMATION: Human neuronal nicotinic acetylcholine
      receptor B2
<220> FEATURE:
<221> NAME/KEY: variation
<222> LOCATION: (10)
<223> OTHER INFORMATION: n = a or g or t/u or c
<220> FEATURE:
<221> NAME/KEY: variation
<222> LOCATION: (18)
<223> OTHER INFORMATION: n = a or g or t/u or c

<400> SEQUENCE: 23
ttcagcaccn cggagagngc c                                      21

<210> SEQ ID NO 24
<211> LENGTH: 21
<212> TYPE: DNA
<213> ORGANISM: Rattus rattus
<220> FEATURE:
<221> NAME/KEY: misc_structure
<222> LOCATION: (1)..(21)
<223> OTHER INFORMATION: Rat neuronal nicotinic acetylcholine
      receptor B2
<220> FEATURE:
<221> NAME/KEY: variation
<222> LOCATION: (10)
<223> OTHER INFORMATION: n = a or g or t/u or c
<220> FEATURE:
<221> NAME/KEY: variation
<222> LOCATION: (18)
<223> OTHER INFORMATION: n = a or g or t/u or c

<400> SEQUENCE: 24
ttcagcaccn cggagagngt c                                      21

<210> SEQ ID NO 25
<211> LENGTH: 21
<212> TYPE: DNA
<213> ORGANISM: Homo sapiens
<220> FEATURE:
<221> NAME/KEY: misc_structure
<222> LOCATION: (1)..(21)
<223> OTHER INFORMATION: Human NMDA receptor (NR1-1)
<220> FEATURE:
<221> NAME/KEY: variation
<222> LOCATION: (10)
<223> OTHER INFORMATION: n = a or g or t/u or c
<220> FEATURE:
<221> NAME/KEY: variation
<222> LOCATION: (18)
<223> OTHER INFORMATION: n = a or g or t/u or c
```

-continued

```
<400> SEQUENCE: 25
ttcagcaccn cggagagngc c                                              21

<210> SEQ ID NO 26
<211> LENGTH: 21
<212> TYPE: DNA
<213> ORGANISM: Rattus rattus
<220> FEATURE:
<221> NAME/KEY: misc_structure
<222> LOCATION: (1)..(21)
<223> OTHER INFORMATION: Rat NMDA receptor (NR1-1)
<220> FEATURE:
<221> NAME/KEY: variation
<222> LOCATION: (10)
<223> OTHER INFORMATION: n = a or g or t/u or c
<220> FEATURE:
<221> NAME/KEY: variation
<222> LOCATION: (18)
<223> OTHER INFORMATION: n = a or g or t/u or c

<400> SEQUENCE: 26
ttcagcaccn cggagagnat c                                              21

<210> SEQ ID NO 27
<211> LENGTH: 21
<212> TYPE: DNA
<213> ORGANISM: Homo sapiens
<220> FEATURE:
<221> NAME/KEY: misc_structure
<222> LOCATION: (1)..(21)
<223> OTHER INFORMATION: Human synapsin I
<220> FEATURE:
<221> NAME/KEY: variation
<222> LOCATION: (10)
<223> OTHER INFORMATION: n = a or g or t/u or c
<220> FEATURE:
<221> NAME/KEY: variation
<222> LOCATION: (18)
<223> OTHER INFORMATION: n = a or g or t/u or c

<400> SEQUENCE: 27
ttcagcaccn cggagagngc c                                              21

<210> SEQ ID NO 28
<211> LENGTH: 21
<212> TYPE: DNA
<213> ORGANISM: Rattus rattus
<220> FEATURE:
<221> NAME/KEY: misc_structure
<222> LOCATION: (1)..(21)
<223> OTHER INFORMATION: Rat synapsin I
<220> FEATURE:
<221> NAME/KEY: variation
<222> LOCATION: (10)
<223> OTHER INFORMATION: n = a or g or t/u or c
<220> FEATURE:
<221> NAME/KEY: variation
<222> LOCATION: (18)
<223> OTHER INFORMATION: n = a or g or t/u or c

<400> SEQUENCE: 28
tttagtaccn cggagagngc c                                              21

<210> SEQ ID NO 29
<211> LENGTH: 31
<212> TYPE: DNA
<213> ORGANISM: Rattus rattus
<220> FEATURE:
<221> NAME/KEY: misc_structure
<222> LOCATION: (1)..(21)
<223> OTHER INFORMATION: Rat somatstatin activating factor
```

```
<220> FEATURE:
<221> NAME/KEY: variation
<222> LOCATION: (15)
<223> OTHER INFORMATION: n = a or g or t/u or c
<220> FEATURE:
<221> NAME/KEY: variation
<222> LOCATION: (23)
<223> OTHER INFORMATION: n = a or g or t/u or c

<400> SEQUENCE: 29
gttctttcag caccncggag agngcacgca g                               31

<210> SEQ ID NO 30
<211> LENGTH: 31
<212> TYPE: DNA
<213> ORGANISM: Homo sapiens
<220> FEATURE:
<221> NAME/KEY: misc_structure
<222> LOCATION: (1)..(31)
<223> OTHER INFORMATION: Human neural cell adhesion molecule (NCAM)
<220> FEATURE:
<221> NAME/KEY: variation
<222> LOCATION: (15)
<223> OTHER INFORMATION: n = a or g or t/u or c
<220> FEATURE:
<221> NAME/KEY: variation
<222> LOCATION: (23)
<223> OTHER INFORMATION: n = a or g or t/u or c

<400> SEQUENCE: 30
gcgatttcag caccngggag agngaacctg g                               31

<210> SEQ ID NO 31
<211> LENGTH: 31
<212> TYPE: DNA
<213> ORGANISM: Mus musculus
<220> FEATURE:
<221> NAME/KEY: misc_structure
<222> LOCATION: (1)..(31)
<223> OTHER INFORMATION: Mouse natiuretic peptide
<220> FEATURE:
<221> NAME/KEY: variation
<222> LOCATION: (15)
<223> OTHER INFORMATION: n = a or g or t/u or c
<220> FEATURE:
<221> NAME/KEY: variation
<222> LOCATION: (23)
<223> OTHER INFORMATION: n = a or g or t/u or c

<400> SEQUENCE: 31
taaacttcag caccnaggag agncgccgag g                               31

<210> SEQ ID NO 32
<211> LENGTH: 31
<212> TYPE: DNA
<213> ORGANISM: Rattus rattus
<220> FEATURE:
<221> NAME/KEY: misc_structure
<222> LOCATION: (1)..(31)
<223> OTHER INFORMATION: Rat adenine phosphoribosyltransferase
<220> FEATURE:
<221> NAME/KEY: variation
<222> LOCATION: (15)
<223> OTHER INFORMATION: n = a or g or t/u or c
<220> FEATURE:
<221> NAME/KEY: variation
<222> LOCATION: (23)
<223> OTHER INFORMATION: n = a or g or t/u or c

<400> SEQUENCE: 32
gctgagtcag gaccntggag agngcctgac c                               31
```

```
<210> SEQ ID NO 33
<211> LENGTH: 31
<212> TYPE: DNA
<213> ORGANISM: Bos taurus
<220> FEATURE:
<221> NAME/KEY: misc_structure
<222> LOCATION: (1)..(31)
<223> OTHER INFORMATION: Bovine P-450
<220> FEATURE:
<221> NAME/KEY: variation
<222> LOCATION: (15)
<223> OTHER INFORMATION: n = a or g or t/u or c
<220> FEATURE:
<221> NAME/KEY: variation
<222> LOCATION: (23)
<223> OTHER INFORMATION: n = a or g or t/u or c

<400> SEQUENCE: 33
agttcttcag gaccntggag agnggcaggg t                              31

<210> SEQ ID NO 34
<211> LENGTH: 31
<212> TYPE: DNA
<213> ORGANISM: canine distemper virus
<220> FEATURE:
<221> NAME/KEY: misc_structure
<222> LOCATION: (1)..(31)
<223> OTHER INFORMATION: Canine distemper virus L gene
<220> FEATURE:
<221> NAME/KEY: variation
<222> LOCATION: (15)
<223> OTHER INFORMATION: n = a or g or t/u or c
<220> FEATURE:
<221> NAME/KEY: variation
<222> LOCATION: (23)
<223> OTHER INFORMATION: n = a or g or t/u or c

<400> SEQUENCE: 34
tgtctttccg taccncggag agngccagag t                              31

<210> SEQ ID NO 35
<211> LENGTH: 31
<212> TYPE: DNA
<213> ORGANISM: Ovis aries
<220> FEATURE:
<221> NAME/KEY: misc_structure
<222> LOCATION: (1)..(31)
<223> OTHER INFORMATION: Sheep keratin type II
<220> FEATURE:
<221> NAME/KEY: variation
<222> LOCATION: (15)
<223> OTHER INFORMATION: n = a or g or t/u or c
<220> FEATURE:
<221> NAME/KEY: variation
<222> LOCATION: (23)
<223> OTHER INFORMATION: n = a or g or t/u or c

<400> SEQUENCE: 35
atgtgatcag caccncggag agnggcatga g                              31

<210> SEQ ID NO 36
<211> LENGTH: 31
<212> TYPE: DNA
<213> ORGANISM: Mus musculus
<220> FEATURE:
<221> NAME/KEY: misc_structure
<222> LOCATION: (1)..(31)
<223> OTHER INFORMATION: Mouse alpha skeletal actin
<220> FEATURE:
<221> NAME/KEY: variation
<222> LOCATION: (15)
<223> OTHER INFORMATION: n = a or g or t/u or c
```

```
<220> FEATURE:
<221> NAME/KEY: variation
<222> LOCATION: (23)
<223> OTHER INFORMATION: n = a or g or t/u or c

<400> SEQUENCE: 36
gcttcggcag caccncggcg agngccgcca g                              31

<210> SEQ ID NO 37
<211> LENGTH: 31
<212> TYPE: DNA
<213> ORGANISM: Homo sapiens
<220> FEATURE:
<221> NAME/KEY: misc_structure
<222> LOCATION: (1)..(31)
<223> OTHER INFORMATION: Human T-cell receptor beta subunit
<220> FEATURE:
<221> NAME/KEY: variation
<222> LOCATION: (15)
<223> OTHER INFORMATION: n = a or g or t/u or c
<220> FEATURE:
<221> NAME/KEY: variation
<222> LOCATION: (23)
<223> OTHER INFORMATION: n = a or g or t/u or c

<400> SEQUENCE: 37
gtaccgtcag caacntggag agngcctgac a                              31

<210> SEQ ID NO 38
<211> LENGTH: 31
<212> TYPE: DNA
<213> ORGANISM: Sus scrofa
<220> FEATURE:
<221> NAME/KEY: misc_structure
<222> LOCATION: (1)..(31)
<223> OTHER INFORMATION: Pig alpha lactalbumin
<220> FEATURE:
<221> NAME/KEY: variation
<222> LOCATION: (15)
<223> OTHER INFORMATION: n = a or g or t/u or c
<220> FEATURE:
<221> NAME/KEY: variation
<222> LOCATION: (23)
<223> OTHER INFORMATION: n = a or g or t/u or c

<400> SEQUENCE: 38
tgtctttcag caccngggag agntcacatt t                              31

<210> SEQ ID NO 39
<211> LENGTH: 2042
<212> TYPE: DNA
<213> ORGANISM: Homo sapiens
<220> FEATURE:
<221> NAME/KEY: gene
<222> LOCATION: (1)..(2042)
<223> OTHER INFORMATION: Human NSRF (partial)
<220> FEATURE:
<221> NAME/KEY: variation
<222> LOCATION: (15)
<223> OTHER INFORMATION: n = a or g or t/u or c
<220> FEATURE:
<221> NAME/KEY: variation
<222> LOCATION: (23)
<223> OTHER INFORMATION: n = a or g or t/u or c

<400> SEQUENCE: 39
gaattccggg gccccagacc ctggcggcgg ctgcggcagc cgagacggca gggcgaggcc      60
cggaggcctg agcaccctct gcagcccac tcctgggcct tcttggtcca cgacggcccc     120
agcacccaac tttaccaccc tcccccacct ctccccgaa actccagcaa caagaaaag      180
```

-continued

```
tagtcggaga aggagcggcg actcagggtc gcccgcccct cctcaccgag gaaggccgaa    240
tacagttatg ccacccagg taatggggca gtcttctgga ggaggagggc tgtttaccag    300
cagtggcaac attggaatgg ccctgcctaa cgacatgtat gacttgcatg acctttccaa   360
agctgaactg gccgcacctc agcttattat gctggcaaat gtggccttaa ctggggaagt   420
aaatggcagc tgctgtgatt acctggtcgg tgaagaaaga cagatggcag aactgatgcc   480
gttggggata caacttttc agatagtgaa gaaggagaag gacttgaaga gtctgctgat    540
ataaaaggtg aacctcatgg actggaaaac atggaactga gaagtttgga actcagcgtc   600
gtagaacctc agcctgtatt tgaggcatca ggtgctccag atatttacag ttcaaataaa   660
gatcttcccc ctgaaacacc tggagcggag gacaaaggca agagctcgaa gaccaaaccc   720
tttcgctgta agccatgcca atatgaagca gaatctgaag aacagtttgt gcatcacatc   780
agagttcaca gtgctaagaa atttttttgtg gaagagagtg cagagaagca ggcaaaagcc   840
agggaatctg gctcttccac tgcagaagag ggagattct ccaagggccc cattcgctgt   900
gaccgctgcg gctacaatac taatcgatat gatcactata cagcacacct gaaacaccac   960
accagagctg gggataatga gcgagtctac aagtgtatca tttgcacata cacaacagtg  1020
agcgagtatc actggaggaa acatttaaga accattttc caaggaaagt atacacatgt   1080
ggaaaatgca actattttc agacagaaaa acaattatg ttcagcatgt tagaactcat   1140
acaggagaac gcccatataa atgtgaactt tgtccttact caagttctca gaagactcat   1200
ctaactagac atatgcgtac tcattcaggt gagaagccat ttaaatgtga tcagtgcagt   1260
tatgtggcct ctaatcaaca tgaagtaacc cgccatgcaa gacaggttca caatgggcct   1320
aaacctctta attgcccaca ctgtgattac aaaacagcag atagaagcaa cttcaaaaaa   1380
catgtagagc tacatgtgaa cccacggcag ttcaattgcc ctgtatgtga ctatgcagct   1440
tccaagaagt gtaatctaca gtatcacttc aaatctaagc atcctacttg tcctaataaa   1500
acaatggatg tctcaaaagt gaaactaaag aaaaccaaaa acgagaggc tgacttgcct   1560
gataatatta ccaatgaaaa aacagaaata gaacaaacaa aaataaaagg ggatgtggct   1620
ggaaagaaaa atgaaaagtc cgtcaaagca gagaaaagag atgtctcaaa agagaaaaag   1680
ccttctaata atgtgtcagt gatccaggtg actaccagaa ctcgaaaatc agtaacagag   1740
gtgaaagaga tggatgtgca tacaggaagc aattcagaaa aattcagtaa aactaagaaa   1800
agcaaaagga agctggaagt tgacagccat tctttacatg gtcctgtgaa tgatgaggaa   1860
tcttcaacaa aaagaaaaa gaaggtagaa agcaaatcca aaataatag tcaggaagtg   1920
ccaaggggtg acagcaaagt ggaggagaat aaaaagcaaa atacttgcat gaaaaaaagt   1980
acaaagaaga aaactctgaa aaataaatca agtaagaaaa gcagtaagcc ttctcggaat   2040
tc                                                                  2042
```

<210> SEQ ID NO 40
<211> LENGTH: 676
<212> TYPE: PRT
<213> ORGANISM: Homo sapiens
<220> FEATURE:
<221> NAME/KEY: CHAIN
<222> LOCATION: (1)..(676)
<223> OTHER INFORMATION: Human NSRF (partial)

<400> SEQUENCE: 40

```
Gly Ala Pro Asp Pro Gly Gly Gly Cys Gly Ser Arg Asp Gly Arg Ala
  1               5                  10                  15
```

-continued

```
Arg Pro Gly Gly Leu Ser Thr Leu Cys Ser Pro Thr Pro Gly Pro Ser
             20                  25                  30

Trp Ser Thr Thr Ala Pro Ala Pro Asn Phe Thr Thr Leu Pro His Leu
         35                  40                  45

Ser Pro Glu Thr Pro Ala Thr Lys Lys Ser Ser Arg Arg Arg Ser Gly
 50                  55                  60

Asp Ser Gly Ser Pro Ala Pro Pro His Arg Gly Arg Pro Asn Thr Val
 65                  70                  75                  80

Met Ala Thr Gln Val Met Gly Gln Ser Ser Gly Gly Gly Leu Phe
                 85                  90                  95

Thr Ser Ser Gly Asn Ile Gly Met Ala Leu Pro Asn Asp Met Tyr Asp
             100                 105                 110

Leu His Asp Leu Ser Lys Ala Glu Leu Ala Ala Pro Gln Leu Ile Met
         115                 120                 125

Leu Ala Asn Val Ala Leu Thr Gly Glu Val Asn Gly Ser Cys Cys Asp
     130                 135                 140

Tyr Leu Val Gly Glu Glu Arg Gln Met Ala Glu Leu Met Pro Val Gly
145                 150                 155                 160

Asp Asn Asn Phe Ser Asp Ser Glu Gly Glu Gly Leu Glu Glu Ser
                 165                 170                 175

Ala Asp Ile Lys Gly Glu Pro His Gly Leu Glu Asn Met Glu Leu Arg
             180                 185                 190

Ser Leu Glu Leu Ser Val Val Glu Pro Gln Pro Val Phe Glu Ala Ser
         195                 200                 205

Gly Ala Pro Asp Ile Tyr Ser Ser Asn Lys Asp Leu Pro Pro Glu Thr
     210                 215                 220

Pro Gly Ala Glu Asp Lys Gly Lys Ser Ser Lys Thr Lys Pro Phe Arg
225                 230                 235                 240

Cys Lys Pro Cys Gln Tyr Glu Ala Glu Ser Glu Glu Gln Phe Val His
                 245                 250                 255

His Ile Arg Val His Ser Ala Lys Lys Phe Phe Val Glu Glu Ser Ala
             260                 265                 270

Glu Lys Gln Ala Lys Ala Arg Glu Ser Gly Ser Ser Thr Ala Glu Glu
         275                 280                 285

Gly Asp Phe Ser Lys Gly Pro Ile Arg Cys Asp Arg Cys Gly Tyr Asn
     290                 295                 300

Thr Asn Arg Tyr Asp His Tyr Thr Ala His Leu Lys His His Thr Arg
305                 310                 315                 320

Ala Gly Asp Asn Glu Arg Val Tyr Lys Cys Ile Ile Cys Thr Tyr Thr
                 325                 330                 335

Thr Val Ser Glu Tyr His Trp Arg Lys His Leu Arg Asn His Phe Pro
             340                 345                 350

Arg Lys Val Tyr Thr Cys Gly Lys Cys Asn Tyr Phe Ser Asp Arg Lys
         355                 360                 365

Asn Asn Tyr Val Gln His Val Arg Thr His Thr Gly Glu Arg Pro Tyr
     370                 375                 380

Lys Cys Glu Leu Cys Pro Tyr Ser Ser Ser Gln Lys Thr His Leu Thr
385                 390                 395                 400

Arg His Met Arg Thr His Ser Gly Glu Lys Pro Phe Lys Cys Asp Gln
                 405                 410                 415

Cys Ser Tyr Val Ala Ser Asn Gln His Glu Val Thr Arg His Ala Arg
             420                 425                 430

Gln Val His Asn Gly Pro Lys Pro Leu Asn Cys Pro His Cys Asp Tyr
```

-continued

```
                   435                 440                 445

Lys Thr Ala Asp Arg Ser Asn Phe Lys Lys His Val Glu Leu His Val
            450                 455                 460

Asn Pro Arg Gln Phe Asn Cys Pro Val Cys Asp Tyr Ala Ala Ser Lys
465                 470                 475                 480

Lys Cys Asn Leu Gln Tyr His Phe Lys Ser Lys His Pro Thr Cys Pro
                485                 490                 495

Asn Lys Thr Met Asp Val Ser Lys Val Lys Leu Lys Lys Thr Lys Lys
            500                 505                 510

Arg Glu Ala Asp Leu Pro Asp Asn Ile Thr Asn Glu Lys Thr Glu Ile
            515                 520                 525

Glu Gln Thr Lys Ile Lys Gly Asp Val Ala Gly Lys Lys Asn Glu Lys
            530                 535                 540

Ser Val Lys Ala Glu Lys Arg Asp Val Ser Lys Glu Lys Lys Pro Ser
545                 550                 555                 560

Asn Asn Val Ser Val Ile Gln Val Thr Thr Arg Thr Arg Lys Ser Val
                565                 570                 575

Thr Glu Val Lys Glu Met Asp Val His Thr Gly Ser Asn Ser Glu Lys
            580                 585                 590

Phe Ser Lys Thr Lys Lys Ser Lys Arg Lys Leu Glu Val Asp Ser His
            595                 600                 605

Ser Leu His Gly Pro Val Asn Asp Glu Glu Ser Ser Thr Lys Lys Lys
            610                 615                 620

Lys Lys Val Glu Ser Lys Ser Lys Asn Asn Ser Gln Glu Val Pro Lys
625                 630                 635                 640

Gly Asp Ser Lys Val Glu Glu Asn Lys Lys Gln Asn Thr Cys Met Lys
                645                 650                 655

Lys Ser Thr Lys Lys Lys Thr Leu Lys Asn Lys Ser Ser Lys Lys Ser
            660                 665                 670

Ser Lys Pro Ser
        675

<210> SEQ ID NO 41
<211> LENGTH: 23
<212> TYPE: PRT
<213> ORGANISM: Homo sapiens
<220> FEATURE:
<221> NAME/KEY: DOMAIN
<222> LOCATION: (1)..(23)
<223> OTHER INFORMATION: Zinc finger region Z1

<400> SEQUENCE: 41

Phe Arg Cys Lys Pro Cys Gln Tyr Glu Ala Glu Ser Glu Glu Gln Phe
1               5                   10                  15

Val His His Ile Arg Val His
            20

<210> SEQ ID NO 42
<211> LENGTH: 32
<212> TYPE: PRT
<213> ORGANISM: Homo sapiens
<220> FEATURE:
<221> NAME/KEY: DOMAIN
<222> LOCATION: (1)..(32)
<223> OTHER INFORMATION: Zinc finger region Z2

<400> SEQUENCE: 42

Ile Arg Cys Asp Arg Cys Gly Tyr Asn Thr Asn Arg Tyr Asp His Tyr
1               5                   10                  15
```

```
Thr Ala His Leu Lys His His Thr Arg Ala Gly Asp Asn Glu Arg Val
            20                  25                  30

<210> SEQ ID NO 43
<211> LENGTH: 28
<212> TYPE: PRT
<213> ORGANISM: Homo sapiens
<220> FEATURE:
<221> NAME/KEY: DOMAIN
<222> LOCATION: (1)..(24)
<223> OTHER INFORMATION: Zinc finger region Z3
<220> FEATURE:
<221> NAME/KEY: DOMAIN
<222> LOCATION: (1)..(28)
<223> OTHER INFORMATION: Zinc finger region Z3

<400> SEQUENCE: 43

Tyr Lys Cys Ile Ile Cys Thr Tyr Thr Thr Val Ser Glu Tyr His Trp
  1               5                  10                  15

Arg Lys His Leu Arg Asn His Phe Pro Arg Lys Val
            20                  25

<210> SEQ ID NO 44
<211> LENGTH: 28
<212> TYPE: PRT
<213> ORGANISM: Homo sapiens
<220> FEATURE:
<221> NAME/KEY: DOMAIN
<222> LOCATION: (1)..(28)
<223> OTHER INFORMATION: Zinc finger region Z4

<400> SEQUENCE: 44

Tyr Thr Cys Gly Lys Cys Asn Tyr Phe Ser Asp Arg Lys Asn Asn Tyr
  1               5                  10                  15

Val Gln His Val Arg Thr His Thr Gly Glu Arg Pro
            20                  25

<210> SEQ ID NO 45
<211> LENGTH: 28
<212> TYPE: PRT
<213> ORGANISM: Homo sapiens
<220> FEATURE:
<221> NAME/KEY: DOMAIN
<222> LOCATION: (1)..(28)
<223> OTHER INFORMATION: Zinc finger domain Z5

<400> SEQUENCE: 45

Tyr Lys Cys Glu Leu Cys Pro Tyr Ser Ser Ser Gln Lys Thr His Leu
  1               5                  10                  15

Thr Arg His Met Arg Thr His Ser Gly Glu Lys Pro
            20                  25

<210> SEQ ID NO 46
<211> LENGTH: 29
<212> TYPE: PRT
<213> ORGANISM: Homo sapiens
<220> FEATURE:
<221> NAME/KEY: DOMAIN
<222> LOCATION: (1)..(29)
<223> OTHER INFORMATION: Zinc finger domain Z6

<400> SEQUENCE: 46

Phe Lys Cys Asp Gln Cys Ser Tyr Val Ala Ser Asn Gln His Glu Val
  1               5                  10                  15

Thr Arg His Ala Arg Gln Val His Asn Gly Pro Lys Pro
            20                  25
```

<210> SEQ ID NO 47
<211> LENGTH: 28
<212> TYPE: PRT
<213> ORGANISM: Homo sapiens
<220> FEATURE:
<221> NAME/KEY: DOMAIN
<222> LOCATION: (1)..(28)
<223> OTHER INFORMATION: Zinc finger domain Z7

<400> SEQUENCE: 47

Leu Asn Cys Pro His Cys Asp Tyr Lys Thr Ala Asp Arg Ser Asn Phe
 1               5                  10                  15

Lys Lys His Val Glu Leu His Val Asn Pro Arg Gln
            20                  25

<210> SEQ ID NO 48
<211> LENGTH: 24
<212> TYPE: PRT
<213> ORGANISM: Homo sapiens
<220> FEATURE:
<221> NAME/KEY: DOMAIN
<222> LOCATION: (1)..(24)
<223> OTHER INFORMATION: Zinc finger domain Z8

<400> SEQUENCE: 48

Phe Asn Cys Pro Val Cys Asp Tyr Ala Ala Ser Lys Lys Cys Asn Leu
 1               5                  10                  15

Gln Tyr His Phe Lys Ser Lys His
            20

<210> SEQ ID NO 49
<211> LENGTH: 4057
<212> TYPE: DNA
<213> ORGANISM: Homo sapiens
<220> FEATURE:
<221> NAME/KEY: gene
<222> LOCATION: (1)..(4057)
<223> OTHER INFORMATION: Human NSRF

<400> SEQUENCE: 49
ttcggacgag gcgggcgggc ggcgacggcg cgggcgggtg cgcggcgcag cgtcctgtgc      60
tggaatgtgc ggctcccgcg agctcgcggc gcagcagcag aagaccgagg agcgccgccg     120
aggccgcggg ccccagaccc gggcggccgg gaccgcagcg acggcagaac cagggccggc     180
ggtctgatcc cgctccgcga tcgcaccccg ggatctcgag ggcctcgacg cccaactttt     240
ccccgctctc cctcccctcc cctccccga aagtccagca acaaagaaaa ggagttggag      300
cggcgrcgac gcggggtgg cggaccgtgg gcgcacagtt cagaggagta cagttatggc      360
cacccaggtg atgggcagt cttctggagg aggcagtctc ttcaacaaca gtgccaacat      420
gggcatggsc ttaaccaacg acatgtacga cctgcacgag ctctcgaaag ctgaactggc      480
agcccctcag ctcatcatgt tagccaacgt ggccctgacg ggggaggcaa gcggcagctg      540
ctgcgattac ctggtcggtg aagagaggca gatggccgaa ttgatgcccg tgggagacaa      600
ccacttctca gaaagtgaag gagaaggcct ggaagagtcg gctgacctca aagggctgga      660
aaacatggaa ctgggaagtt tggagctaag tgctgtagaa cccagcccg tatttgaagc      720 ctcagctgcc ccagaaatat acagcgccaa taaagatccc gctccagaaa caccgtggc      780 ggaagacaaa tgcaggagtt ctaaggccaa gcccttccgg tgtaagcctt gccagtacga     840
agccgaatct gaagagcagt tgtgcatca catccggatt cacagcgcta agaagttctt     900

-continued

```
tgtggaggaa agtgcagaga aacaggccaa agcctgggag tcggggtcgt ctccggccga    960
agagggcgag ttctccaaag gccccatccg ctgtgaccgc tgtggctaca ataccaaccg   1020
gtatgaccac tacatggcac acctgaagca ccacctgcga gctggcgaga acgagcgcat   1080
ctacaagtgc atcatctgca cgtacacgac ggtcagcgag taccactgga ggaaacacct   1140
gagaaaccat ttccccagga aagtctacac ctgcagcaag tgcaactact tctcagacag   1200
aaaaaataac tacgttcagc acgtgcgaac tcacacagga aacgcccgt ataaatgtga    1260 actttgtcct tactcaagct ctcagaagac tcatctaacg cgacacatgc ggactcattc   1320
aggtgagaag ccatttaaat gtgatgagtg caattatgtg gcctctaatc agcatgaagt   1380
gacccgacat gcaagacagg ttcacaacgg gcctaaacct cttaattgcc cgcactgtga   1440
ctacaaaaca gcagatagaa gcaacttcaa aaagcacgtg gagctgcatg ttaacccacg   1500
gcagttcaac tgccccgtgt gtgactacgc ggcttctaag aagtgtaatc tacaatacca   1560
tttcaaatct aagcatccca cctgtcccag caaaacaatg gatgtctcca agtgaagct    1620 aaagaaaacc aaaagagag aggctgacct gcttaataac gccgtcagca acgagaagat    1680
ggagaatgag caaacaaaaa caaggggga tgtgtctggg aagaagaacg agaaacctgt    1740
aaaagctgtg ggaaagatg cttcaaaaga gaagaagcct ggtagcagtg tctcagtggt    1800
ccaggtaact accaggactc ggaagtcagc ggtggcggcg gagactaaag cagcagaggt   1860
gaaacacaca gacggacaaa caggaaacca tccagaaaag ccctgtaaag ccaagaaaaa   1920 caaagaaag aaggatgctg aggcccatcc ctccgacagg cctgtgaacg agggaccagt    1980
gacaaaaaag aaaagaagt ctgagtgcaa atcaaaaatc agtaccaacg tgccaaaggg    2040
cggcggccga gcggaggaga ggccgggggt caagaagcaa agcgcttccc ttaagaaagg   2100 cacaagaag acgccgccca agacaaagac aagtaaaaaa ggtggcaaac ttgctcccac    2160
ggagcctgcc cctcccacgg ggcttgccga gatggaacct ctcccacgg agccttccca    2220 gaaggaacca cctcccagta tggagcctcc ctgccccgag gagctgcctc aggccgagcc   2280
acctcctatg gaggattgtc agaaggagct gccttctccc gtggagcccg ctcagattga   2340
ggttgctcag acggccccta cgcaggttca ggaggagccc cctcctgtct cggagccacc   2400
tcgggtgaag ccaaccaaaa gatcatctct ccggaaagac agagcagaga aggagctgag   2460
cctgctgagt gagatggcgc ggcaggagca ggtcctcatg gggggttggct tggtgcctgt   2520 tagagacagc aagcttctga agggaaacaa gagcgcccag gaccccccag ccccaccgtc   2580
accatcgcca aagggaaact cgagggaaga gacacccaag gaccaagaaa tggtctctga   2640
tggggaagga actatagtat tccctctcaa gaaggaggga ccagaggaag ctggagagag   2700
tccagctgag ttggctgctc tcaaggagtc tgcccgtgtt tcatcctctg aacaaaactc   2760
agccatgcca gagggtggag catcacacag caagtgtcag actggctcct ctgggctttg   2820
tgacgtggac actgagcaga agacagatac tgtccccatg aaagactccg cagcagagcc   2880 agtgtccccct cctaccccaa cagtggaccg tgacgcaggg tcaccagctg tagtggcctc   2940
ccctcctatc acgttggctg aaaacgagtc tcaggaaatt gatgaagatg aaggcatcca   3000
tagccatgat ggaagtgacc tgagtgacaa catgtctgag gggagtgacg actcaggact   3060
gcacggggct cggccgacac caccagaagc tacgtcaaaa aatgggaagg cagggttggc   3120
tggtaaagtg actgagggag agtttgtgtg tattttctgt gatcgttctt ttagaaagga   3180 aaagattat agcaaacacc tcaatcgcca cttggtgaat gtgtacttcc tagaagaagc    3240
agctgaggag caggaggagc aggaggagcg ggaggagcag gagtagctga gcctcgggag   3300
```

-continued

```
aagcaccgtg cagactttgt gagcatgcaa ttttaatttg tagacaaacg caagcttgct    3360
ttaattagtc tccaaggctg agttttcagt aacattcttt ttcttaggac tgtacatcta    3420
tttagtgttt gttgcataaa tcttagcaaa tcctcgggag ttaatgtaag aggacagata    3480
tgtaactagc tcgtgcaggc aggtgcaagg agaagggtaa gatggtggaa cacaccactt    3540
gccttgtctg cctacaacct gttgggtttt cttttcacgg tagttcctaa ttttagtta    3600 cttgtttaga tcgataaaaa ttggcttagt aaattacttg aagaatttgc ctgctttata    3660
taaattaagt tagcacttta cagttycttt agagatgaaa aaaagagat tttaattgga    3720 gagaaattct caacattgga cattgtatct gtccaggtaa ttgcttccta acttgctatc    3780
aatattttgt gtttatatgt taatcgttat aaaaagtgat ttttgttttt tgggtatttt    3840
ttattttggt gcttttctgg cttaagatgt tgcacatggt tcttgttttt gtttcttaa    3900 cctatgcagt taatctccct tcccctgaaa cagcgttgtg ttaaatagta acactataca    3960
gatatatgca tggtttttt ttttgtttgt ttgtttgttt gttttccctt tttggaggga    4020
tgcttttagg cttgtttgcc tcgtsccgaa ttcgata                              4057
```

<210> SEQ ID NO 50
<211> LENGTH: 976
<212> TYPE: PRT
<213> ORGANISM: Homo sapiens
<220> FEATURE:
<221> NAME/KEY: PEPTIDE
<222> LOCATION: (1)..(976)
<223> OTHER INFORMATION: Human NSRF
<220> FEATURE:
<221> NAME/KEY: CHAIN
<222> LOCATION: (1)..(976)
<223> OTHER INFORMATION: Human NSRF

<400> SEQUENCE: 50

```
Met Ala Thr Gln Val Met Gly Gln Ser Ser Gly Gly Ser Leu Phe
  1               5                  10                  15

Asn Asn Ser Ala Asn Met Gly Met Xaa Leu Thr Asn Asp Met Tyr Asp
                 20                  25                  30

Leu His Glu Leu Ser Lys Ala Glu Leu Ala Ala Pro Gln Leu Ile Met
             35                  40                  45

Leu Ala Asn Val Ala Leu Thr Gly Glu Ala Ser Gly Ser Cys Cys Asp
         50                  55                  60

Tyr Leu Val Gly Glu Glu Arg Gln Met Ala Glu Leu Met Pro Val Gly
 65                  70                  75                  80

Asp Asn His Phe Ser Glu Ser Glu Gly Glu Gly Leu Glu Glu Ser Ala
                 85                  90                  95

Asp Leu Lys Gly Leu Glu Asn Met Glu Leu Gly Ser Leu Glu Leu Ser
            100                 105                 110

Ala Val Glu Pro Gln Pro Val Phe Glu Ala Ser Ala Ala Pro Glu Ile
        115                 120                 125

Tyr Ser Ala Asn Lys Asp Pro Ala Pro Glu Thr Pro Val Ala Glu Asp
    130                 135                 140

Lys Cys Arg Ser Ser Lys Ala Lys Pro Phe Arg Cys Lys Pro Cys Gln
145                 150                 155                 160

Tyr Glu Ala Glu Ser Glu Glu Gln Phe Val His His Ile Arg Ile His
                165                 170                 175

Ser Ala Lys Lys Phe Phe Val Glu Ser Ala Glu Lys Gln Ala Lys
            180                 185                 190
```

-continued

```
Ala Trp Glu Ser Gly Ser Ser Pro Ala Glu Glu Gly Glu Phe Ser Lys
        195                 200                 205

Gly Pro Ile Arg Cys Asp Arg Cys Gly Tyr Asn Thr Asn Arg Tyr Asp
    210                 215                 220

His Tyr Met Ala His Leu Lys His His Leu Arg Ala Gly Glu Asn Glu
225                 230                 235                 240

Arg Ile Tyr Lys Cys Ile Ile Cys Thr Tyr Thr Thr Val Ser Glu Tyr
                245                 250                 255

His Trp Arg Lys His Leu Arg Asn His Phe Pro Arg Lys Val Tyr Thr
            260                 265                 270

Cys Ser Lys Cys Asn Tyr Phe Ser Asp Arg Lys Asn Asn Tyr Val Gln
        275                 280                 285

His Val Arg Thr His Thr Gly Glu Arg Pro Tyr Lys Cys Glu Leu Cys
    290                 295                 300

Pro Tyr Ser Ser Ser Gln Lys Thr His Leu Thr Arg His Met Arg Thr
305                 310                 315                 320

His Ser Gly Glu Lys Pro Phe Lys Cys Asp Glu Cys Asn Tyr Val Ala
                325                 330                 335

Ser Asn Gln His Glu Val Thr Arg His Ala Arg Gln Val His Asn Gly
            340                 345                 350

Pro Lys Pro Leu Asn Cys Pro His Cys Asp Tyr Lys Thr Ala Asp Arg
        355                 360                 365

Ser Asn Phe Lys Lys His Val Glu Leu His Val Asn Pro Arg Gln Phe
    370                 375                 380

Asn Cys Pro Val Cys Asp Tyr Ala Ala Ser Lys Lys Cys Asn Leu Gln
385                 390                 395                 400

Tyr His Phe Lys Ser Lys His Pro Thr Cys Pro Ser Lys Thr Met Asp
                405                 410                 415

Val Ser Lys Val Lys Leu Lys Thr Lys Lys Arg Glu Ala Asp Leu
            420                 425                 430

Leu Asn Asn Ala Val Ser Asn Glu Lys Met Glu Asn Glu Gln Thr Lys
        435                 440                 445

Thr Lys Gly Asp Val Ser Gly Lys Lys Asn Glu Lys Pro Val Lys Ala
    450                 455                 460

Val Gly Lys Asp Ala Ser Lys Glu Lys Lys Pro Gly Ser Ser Val Ser
465                 470                 475                 480

Val Val Gln Val Thr Thr Arg Thr Arg Lys Ser Ala Val Ala Ala Glu
                485                 490                 495

Thr Lys Ala Ala Glu Val Lys His Thr Asp Gly Gln Thr Gly Asn Asn
            500                 505                 510

Pro Glu Lys Pro Cys Lys Ala Lys Lys Asn Lys Arg Lys Lys Asp Ala
        515                 520                 525

Glu Ala His Pro Ser Asp Glu Pro Val Asn Glu Gly Pro Val Thr Lys
    530                 535                 540

Lys Lys Lys Lys Ser Glu Cys Lys Ser Lys Ile Ser Thr Asn Val Pro
545                 550                 555                 560

Lys Gly Gly Gly Arg Ala Glu Glu Arg Pro Gly Val Lys Lys Gln Ser
                565                 570                 575

Ala Ser Leu Lys Lys Gly Thr Lys Thr Pro Pro Lys Thr Lys Thr
            580                 585                 590

Ser Lys Lys Gly Gly Lys Leu Ala Pro Thr Glu Pro Ala Pro Pro Thr
        595                 600                 605

Gly Leu Ala Glu Met Glu Pro Ser Pro Thr Glu Pro Ser Gln Lys Glu
```

```
                    610                  615                  620
Pro Pro Pro Ser Met Glu Pro Pro Cys Pro Glu Glu Leu Pro Gln Ala
625                 630                  635                  640
Glu Pro Pro Pro Met Glu Asp Cys Gln Lys Glu Leu Pro Ser Pro Val
                    645                  650                  655
Glu Pro Ala Gln Ile Glu Val Ala Gln Thr Ala Pro Thr Gln Val Gln
                660                  665                  670
Glu Glu Pro Pro Pro Val Ser Glu Pro Pro Arg Val Lys Pro Thr Lys
                675                  680                  685
Arg Ser Ser Leu Arg Lys Asp Arg Ala Glu Lys Glu Leu Ser Leu Leu
690                 695                  700
Ser Glu Met Ala Arg Gln Glu Gln Val Leu Met Gly Val Gly Leu Val
705                 710                  715                  720
Pro Val Arg Asp Ser Lys Leu Leu Lys Gly Asn Lys Ser Ala Gln Asp
                725                  730                  735
Pro Pro Ala Pro Pro Ser Pro Ser Pro Lys Gly Asn Ser Arg Glu Glu
                740                  745                  750
Thr Pro Lys Asp Gln Glu Met Val Ser Asp Gly Glu Gly Thr Ile Val
                755                  760                  765
Phe Pro Leu Lys Lys Gly Gly Pro Glu Glu Ala Gly Glu Ser Pro Ala
770                 775                  780
Glu Leu Ala Ala Leu Lys Glu Ser Ala Arg Val Ser Ser Glu Gln
785                 790                  795                  800
Asn Ser Ala Met Pro Glu Gly Gly Ala Ser His Ser Lys Cys Gln Thr
                805                  810                  815
Gly Ser Ser Gly Leu Cys Asp Val Asp Thr Glu Gln Lys Thr Asp Thr
                820                  825                  830
Val Pro Met Lys Asp Ser Ala Ala Glu Pro Val Ser Pro Pro Thr Pro
                835                  840                  845
Thr Val Asp Arg Asp Ala Gly Ser Pro Ala Val Val Ala Ser Pro Pro
                850                  855                  860
Ile Thr Leu Ala Glu Asn Glu Ser Gln Glu Ile Asp Glu Asp Glu Gly
865                 870                  875                  880
Ile His Ser His Asp Gly Ser Asp Leu Ser Asp Asn Met Ser Glu Gly
                885                  890                  895
Ser Asp Asp Ser Gly Leu His Gly Ala Arg Pro Thr Pro Pro Glu Ala
                900                  905                  910
Thr Ser Lys Asn Gly Lys Ala Gly Leu Ala Gly Lys Val Thr Glu Gly
                915                  920                  925
Glu Phe Val Cys Ile Phe Cys Asp Arg Ser Phe Arg Lys Glu Lys Asp
                930                  935                  940
Tyr Ser Lys His Leu Asn Arg His Leu Val Asn Val Tyr Phe Leu Glu
945                 950                  955                  960
Glu Ala Ala Glu Glu Gln Glu Glu Gln Glu Glu Arg Glu Glu Gln Glu
                965                  970                  975
```

<210> SEQ ID NO 51
<211> LENGTH: 40
<212> TYPE: DNA
<213> ORGANISM: Homo sapiens
<220> FEATURE:
<221> NAME/KEY: primer_bind
<222> LOCATION: (1)..(40)
<223> OTHER INFORMATION: S36

<400> SEQUENCE: 51

```
agctgcaaag ccatttcagc accacggaga gtgcctctgc                                40
```

<210> SEQ ID NO 52
<211> LENGTH: 37
<212> TYPE: DNA
<213> ORGANISM: Homo sapiens
<220> FEATURE:
<221> NAME/KEY: primer_bind
<222> LOCATION: (1)..(37)
<223> OTHER INFORMATION: Na33
<220> FEATURE:
<221> NAME/KEY: variation
<222> LOCATION: (3)
<223> OTHER INFORMATION: n = a or g or t/u or c

<400> SEQUENCE: 52

```
agnattgggt tcagaacca cggacagcac cagagta                                    37
```

<210> SEQ ID NO 53
<211> LENGTH: 39
<212> TYPE: DNA
<213> ORGANISM: Homo sapiens
<220> FEATURE:
<221> NAME/KEY: primer_bind
<222> LOCATION: (1)..(39)
<223> OTHER INFORMATION: Syn
<220> FEATURE:
<221> NAME/KEY: variation
<222> LOCATION: (3)
<223> OTHER INFORMATION: n = a or g or t/u or c

<400> SEQUENCE: 53

```
agnttatgcc agcttcagca ccgcggacag tgccttcca                                 39
```

<210> SEQ ID NO 54
<211> LENGTH: 40
<212> TYPE: DNA
<213> ORGANISM: Homo sapiens
<220> FEATURE:
<221> NAME/KEY: primer_bind
<222> LOCATION: (1)..(40)
<223> OTHER INFORMATION: BDNF
<220> FEATURE:
<221> NAME/KEY: variation
<222> LOCATION: (3)
<223> OTHER INFORMATION: n = a or g or t/u or c

<400> SEQUENCE: 54

```
agnttagagt ccattcagca ccttggacag agccagcgga                                40
```

<210> SEQ ID NO 55
<211> LENGTH: 27
<212> TYPE: DNA
<213> ORGANISM: Homo sapiens
<220> FEATURE:
<221> NAME/KEY: primer_bind
<222> LOCATION: (1)..(27)
<223> OTHER INFORMATION: Ets
<220> FEATURE:
<221> NAME/KEY: variation
<222> LOCATION: (3)
<223> OTHER INFORMATION: n = a or g or t/u or c

<400> SEQUENCE: 55

```
agnttgcgga acggaagcgg aaaccga                                              27
```

NEURON-RESTRICTIVE SILENCER FACTOR PROTEINS

This application is a continuation-in-part of U.S. patent application Ser. No. 08/398,590 filed Mar. 3, 1995 now U.S. Pat. No. 5,935,811.

FIELD OF THE INVENTION

The present invention relates to neuron-restrictive silencer factor proteins, nucleic acids, and antibodies thereto.

BACKGROUND OF THE INVENTION

The molecular basis of neuronal determination and differentiation in vertebrates is not well understood. It other lineages, systematic promoter analysis of cell-type specific genes has led to the identification of genetically essential transcriptional regulators of lineage determination or differentiation L. M. Corcoran, et al., *Genes and Development* 7, 570–582 (1993); S. Li, et al., *Nature* (London) 347, 528–533 (1990); L. Pevny, et al., *Nature* 349, 257–260 (1991). To apply this approach to the development of neurons, the transcriptional regulation of a neuron-specific gene, SCG10, has been previously examined (D. J. Anderson, R. Axel, *Cell* 42, 649–662 (1985). SCG10 is a 22 Kd, membrane-associated phosphoprotein that accumulates in growth cones and is transiently expressed by all developing neurons (R. Stein, N. Mori, K. Matthews, L.-C. Lo, D. J. Anderson, *Neuron* 1, 463–476 (1988); U. K. Shubart, M. D. Banerjce, *J. Eng. DNA* 8, 389–398 (1989)). Upstream regulatory sequences controlling SCG10 transcription have been analyzed using promoter fusion constructs, both in transient cell transfection assays and in transgenic mice (N. Mori, R. Stein, O. Sigmund, D. J. Anderson, *Neuron* 4, 583–594 (1990); C. W. Wuenschell, N. Mori, D. J. Anderson, *Neuron* 4, 595–602 (1990)). These studies revealed that the 5' flanking region can be functionally separated into two regulatory domains: a promoter-proximal region that is active in many cell lines and tissues, and a distal region that selectively represses this transcription in non-neuronal cells. Deletion of the distal region relieves the repression of SCG10 transgenes in non-neuronal tissues, such as liver, in transgenic mice (C. W. Wuenschell, N. Mori, D. J. Anderson, *Neuron* 4, 595–602 (1990); D. J. Vandenbergh, C. W. Wuenschell, N. Mori, D. J. Anderson, *Neuron* 3, 507–518 (1989)). Furthermore, in transient cell transfection assays this distal region could repress transcription from a heterologous promoter in an orientation- and distance-independent manner (N. Mori, R. Stein, O. Sigmund, D. J. Anderson, *Neuron* 4, 583–594 (1990)), satisfying the criteria for a silencer: a sequence analogous to an enhancer but with an opposite effect on transcription (A. H. Brand, L. Breeden, J. Abraham, R. Sternglanz, K. Nasmyth, *Cell* 41, 41–48 (1985)). The finding that neuron-specific gene expression is controlled primarily by selective silencing stands in contrast to most cell type-specific genes studied previously, in which specificity is achieved by lineage-specific enhancer factors (T. Maniatis, S. Goodbourn, J. A. Fischer, *Science* 236, 1237–1245 (1987); P. Mitchell, R. Tjian, *Science* 245, 371–378 (1989); P. F. Johnson, S. L. McKnight, *Annu. Rev. Biochem.* 58, 799–839 (1989); X. He, M. G. Rosenfeld, *Neuron* 7,183–196 (1991)).

A detailed analysis of the SCG10 silencer region identified a ca. 24 bp element necessary and sufficient for silencing (N. Mori, S. Schoenherr, D. J. Vandenbergh, D. J. Anderson, *Neuron* 9, 1–10 (1992)). Interestingly, similar sequence elements were identified in two other neuron-specific genes: the rat type II sodium (NaII) channel and the human synapsin 1 genes (N. Mori, S. Schoenherr, D. J. Vandenbergh, D. J. Anderson, *Neuron* 9, 1–10 (1992); R. A. Maue, S. D. Knaner, R. H. Goodman, G. Mandel, *Neuron* 4, 223–231 (1990); S. D. Kraner, J. A. Chong, H. J. Tsay, G. Mandel, *Neuron* 9, 37–44 (1992); L. Li, T. Suzuki, N. Mori, P. Greengard, *Proceedings of the National Academy of Science (USA)* 90, 1460–1464 (1993)). These sequence elements were shown to possess silencing activity in transfection assays as well, and has been named the neuron-restrictive silencer element (NRSE) (N. Mori, S. Schoenherr, D. J. Vandenbergh, D. J. Anderson, *Neuron* 9, 1–10 (1992)); in the context of the NaII channel gene, it has also been called repressor element 1 (RE1) (S. D. Kraner, J. A. Chong, H. J. Tsay, G. Mandel, *Neuron* 9, 37–44 (1992)).

Using electrophoretic mobility shift assays, the NRSEs in the SCG10, NaII channel and synapsin I genes were all shown to form complexes with a protein(s) present in non-neuronal cell extracts, but absent in neuronal cell extracts (Mori et al., supra), Kraner et al., supra, Li et al., supra). This protein was termed the neuron-restrictive silencer factor (NRSF). Both the SCG10 and the NaII channel NRSEs competed with similar efficacy for NRSF, suggesting that this protein could bind both NRSEs (Mori et al., supra). Moreover, mutations in the NRSE that abolished NRSF binding in vitro eliminated the silencing activity of the NRSE in transient transfection assays. These data implicated NRSF in the lineage-specific repression of at least two neuron-specific genes.

SUMMARY OF THE INVENTION

The present invention provides recombinant NRSF proteins, and isolated or recombinant nucleic acids which encode the NRSF proteins. Also provided are expression vectors which comprise nucleic acid encoding an NRSF protein operably linked to transcriptional and translational regulatory nucleic acid, and host cells which contain the expression vectors.

An additional aspect of the present invention provides methods for producing NRFS proteins which comprise culturing a host cell transformed with an expression vector and causing expression of the nucleic acid encoding the NRSF protein to produce a recombinant NRSF protein.

An additional aspect provides antibodies to the NRSF proteins of the present invention.

BRIEF DESCRIPTION OF THE DRAWINGS

FIGS. 1A, 1B and 1C are tables identifying genes containing NRSEs. (A). Neuronal genes that contain NRSE-like sequences. The genes listed represent, in order, rat SCG10, rat type II sodium channel, human synapsin I, rat brain-derived neurotrophic factor, human glycine receptor subunit, human NMDA receptor subunit (NR1-1), human neuronal nicotinic acetylcholine receptor β2 subunit, chicken middle molecular weight neurofilament, chicken neuron-specific β4 tubulin, human corticotrophin releasing factor (CRF), chicken calbindin, mouse synaptotagmin-4, rat transcription factor HES-3, rat synaptophysin. Sequences for toad gastrin releasing peptide, rat VGF, and a human olfactory receptor also contained consensus NRSEs but are not shown. (B). Interspecies comparison of NRSE-like sequences in neuronal genes. All homologous sequences are present in similar intragenic positions. Mouse and rat synaptotagmin NRSSEs also show similar conservation (not shown). (C). Non-neuronal genes that contain NRSE-like sequences. The genes listed above represent, in order, rat somatostatin activating factor, the human neural cell adhesion molecule, mouse atrial natriuretic peptide, rate adenine phosphoribosyltransferase, bovine P-450, canine distemper virus L gene, sheep keratin type II, mouse α-skeletal actin, pig gamma-fibrinogen, human T-cell receptor beta subunit, and pig α-lactalbumin. UTR: untranslated region. In parts (A) and (C), the genes listed exhibit the top 10 scores in the database search for neuronal and non-neuronal genes, respectively.

FIG. 2 is a table depicting the activity of PC12 cells expressing NRSF. PC12 cells were co-transfected with reporter plasmids and an expression plasmid containing λHZ4. the pCAT3 reporter plasmid consists of the SCG10 proximal region fused to the bacterial CAT enzyme; pCAT3-S36++ consists of pCAT3 with two tandem copies of the S36 NRSE inserted upstream of the SCG10 sequences. The NRSF expression plasmid (pCMV-HZ4) is derived from pCMV-ATG, a modified version of pcDNA3 (Invitrogen) that provides an initiating methionine and a stop codon for the λHZ4 cDNA. To control for non-specific promoter effects, each co-transfection is performed with a constant molar amount of expression plasmid consisting of differing amounts of pCMV-HZ4 and pCMV-ATG. An RSV-LacZ plasmid was included in all transfections to normalize for trasfection efficiency. The activity of each reporter plasmid in the absence of pCMV-HZ4 was normalized to 100% to compare the relative level of repression of each construct. The numbers represent the mean ±SD of two independent experiments performed in duplicate.

FIG. 3 shows that λH1 encoded NRSF protein has the same sequence specificity of DNA binding as native NRSF. ELectrophoretic mobility shift assays were performed using a HeLa cell nuclear extract or the products of a rabbit reticulocyte lysate in vitro transplation reaction programmed with RNA transcribed from a λH1 fusion construct. The probe was a radiolabeled restriction fragment containing two tandem copies of S36. Competitors used were the S36, Na33 and Sm36 oligonucleotides and an oligonucleotide containing an Ets factor binding site (Ets) (22). The large arrowhead marks the λH1 encoded protein DNA complex (lane 1), the small arrowhead marks the NRSF:DNA complex (lane 9). No complexes were formed by an in vitro translation reaction to which no RNA had been added (data not shown).

FIGS. 4A and 4B showsthat antibodies against GST-λH1 recognize the native NRSF:DNA complex. (A) The indicated amounts (in μl) of αGST-λH1 ascites (48) or a control ascites were added to a mobility shift reaction containing HeLa nuclear extract. The competitor was the S36 oligonucleotide present at 300 fold molar excess. The bracket indicates the supershifted NRSF:DNA complex, and the small arrowhead marks in the NRSF:DNA complex. (B) A mobility shift reaction using a rabbit reticulocyte reaction programmed with λ-H1 encoding RNA. The mobility shift reactions were preformed and analyzed as in the upper panel. For supershift experiments, ascites fluid was included during this incubation. The reactions were performed as in FIG. 3, except that the acrylamide gel used for analysis had an 80:1 acrylamide to bis ratio instead of 30:0.8. The bracket indicates the supershifted λH1-encoded protein:DNA complex, and the large arrowhead marks the λH1-encoded protein:DNA complex. Attempts to obtain an quantitative supershift using higher concentrations of antibody were precluded by the inhibition of DNA biding that occurred when the amount of ascites in the SMSA was increased.

FIG. 5 shows that native and recombinant NRSF recognizes NRSE in four different neuron-specific genes. Elec-trophoretic mobility shift assays were preformed using either nuclear extract from HeLa cells (lanes 1–4), to reveal the activity of native NRSF, or using in vitro synthesized NRSF encoded by the λH1 cDNA (lanes 5–8). The labeled probes consisted of restriction fragments containing NRSEs derived for the rat SCG10 gene (SCG10, lanes 1–5); the rat type II sodium channel gene (NaCh, lanes 2 and 6); the human synapsis I gene (Syn, lanes 3 and 7) or the rat brain-derived neurotrophic factor gene (BDNF, lanes 4 and 8). The large arrowhead indicates the specific co-lex obtained with recombinant NRSF; small arrowhead that obtained with native NRSF. Note that the complexes obtained with all four probes are of similar sizes. The complexes obtained using HeLa extracts were partially supershifted with antibody to recombinant NRSF (cf. FIG. 4) (data not shown).

FIGS. 6(A–C) depicts the nucleotide (SEQ ID NO:39) and deduced amino acid sequence (SEQ ID NO:40) of a partial cDNA (λHZ4) for human NRSF (49). The nucleotide sequence is numbered in standard type, and the amino acid sequence in italics. The eight zinc fingers are underlined.

FIGS. 7A and 7B. (A) Schematic diagram of the predicted amino acid sequences from the NRSF cDNA clones. λH1 is the original cDNA isolated by screening the HeLa expression library. λHZ4 was isolated by hybridization to λH1. (B) Alignment of NRSF zinc finger and interfinger sequences. The eight zinc fingers of human NRSF were aligned beginning with the conserved aromatic residue and including the interfinger sequences of fingers z2–7. The consensus for GLI-Krüppel zinc fingers and interfinger sequences is shown for comparison. The conserved tyrosinc residue is boxed.

FIGS. 8A and 8B show the repression of transcription by recombinant NRSF. (A) A representative autoradiogram CAT enzymatic assays from cotransfection experiments in which increasing amounts of an expression plasmid (pCMV-HZ4) encoding a partial NRSF cDNA (clone λHZ4; see FIG. 7A) were cotransfected into PC12 cells together with a CAT reporter plasmid containing two tandem SCG10 NRSEs (pCAT3-S36++)(50). (B) A similar experiment as in (A) except that CAT reporter plasmid (pCAT3) lacked NRSEs. See FIG. 2 for quantification.

FIG. 9 depicts the analysis of NRSF message in neuronal and non-neuronal cell lines. RNase protections assays (51) were performed on 10 μg of total RNA from various cell lines. The two neuronal cell lines were MAH, an immortalized rat sympathoadrenal precursor (52), and PC12, a rat pheochromocytoma (53). The non-neuronal cell lines were: RN22 and JS-1, rat schwannomas (54) S. E. Pfeiffer, B. Betschart, J. Cook, P. E. Mancini, R. J. Morris, in *Glial cell lines* S. Federoff, L. Hertz, Eds. (Academic Press, New York, 1978) pp. 287–346; (55) H. Kimura, W. H. Fischer, D. Schubert, *Nature* 348, 257–260 (1990); NCM-1, an immortalized rat schwann cell precursor (56) L.-C. Lo, S. J. Birren, D. J. Anderson, *Devel. Biol.* 145, 139–153 (1990); C6, a rat CNS flioma (57) S. Kumar, et al., *J. Neurosci. Res.* 27, in press (1990); and RAT1 and mouse C3H1OT1/2(10T), embryonic fibroblast lines. A reaction containing yeast tRNA (tRNA) alone was preformed as a negative control. The probes were derived from mouse NRSF and rat β-actin cDNAs. rNRSF and mNRSF indicate the protected products obtained using RNA from rat or mouse cell lines, respectively. (The size difference between NRSF protected products of the mouse and rat most likely reflects a species difference in the sequence of the target mRNA, resulting in incomplete protection of the mouse probe by the rat transcript.) The autoradiographic exposure for the actin protected products was shorter than for NRSF. In this experiment, the RNase digestion was performed with RNase T1 only.

FIGS. 10A, 10B, 10C and 10D depict the comparison of NRSF and SCG10 mRNA expression by in situ hybridization. Adjacent transverse sections of E12.5 (A,B) and E13.5 (C,D) mouse embryos were hybridized with NRSF (A,C) or SCG10 (B,D) antisence probes. The arrows (A–D) indicate the ventricular zone of the neural tube. The large arrowheads (A–D) indicate the sensory ganglia and the small arrowheads, the sympathetic ganglia (C and D). Control hybridization with NRSF sense probes revealed no specific signal (FIG. 9C and data not shown).

FIGS. 11A, 11B and 11C depict the widespread expession of NRSF mRNA in non-neural tissues. In situ hybridization with an NRSF antisense probe (A,B) was performed on parasaggital sections of an E13.5 mouse embryo. (A) The arrowheads mark two positive tissues, the lung and the kidney; the arrow indicates the liver, which expresses much lower levels of NRSF mRNA (see also FIG. 9). (B) The arrowhead marks the ventricular zone in the telencephalon, the arrow indicates the heart. (C) An adjacent section to (B) was hybridized with an NRSF sense probe as a control for non-specific staining (59).

FIGS. 12A and 12B depict the nucleotide (SEQ ID NO:49) and deduced amino acid sequence (SEQ ID NO:50) of the complete cDNA for human NRSF. The nucleotide sequence is numbered in standard type, and the amino acid sequence in italics. The eight zinc fingers are underlined.

DETAILED DESCRIPTION OF THE INVENTION

The invention provides neuron-restrictive silencer factor (NRSF) nucleic acids and proteins. The NRSF proteins of the invention silence or suppress the expression of neuron-specific genes. Without being bound by theory, it appears that the NRSF protein binds to specific DNA sequences, termed neuron-restrictive silencer elements (NRSE), that function to repress the expression of neuronal genes in non-neuronal cells. Thus, the expression of NRSF prevents a cell from expressing neuronal genes, and thus prevents the cell from becoming a neuron.

The NRSFs of the present invention may be identified in several ways. A NRSF nucleic acid or NRSF protein is initially identified by substantial nucleic acid and/or amino acid sequence homology to the sequences shown in FIGS. 6 and 12. Such homology can be based upon the overall nucleic acid or amino acid sequence.

As used herein, a protein is a "NRSF protein" if it contains a sequence having homology to the amino acid sequences shown in FIGS. 6 and 12. FIG. 12 depicts the complete mouse sequence, but it is to be understood that the sequence shown in FIG. 6 is a partial sequence of the human NRSF protein, and that both upstream and downstream sequence exists in the full length protein. Accordingly, proteins which contain "overlap" regions with the sequence shown in FIG. 6 are NRSF proteins if the area of overlap has homology to the sequence shown in FIG. 6. Alternatively, NRSF proteins which are contained within the sequence of FIG. 6 will also have homology to FIG. 6. The homology to FIGS. 6 and 12 is preferably greater than about 50%, more preferably greater than about 70% and most preferably greater than 85%. In some embodiments the homology will be as high as about 90 to 95 or 98%. This homology will be determined using standard techniques known in the art, such as the Best Fit sequence program described by Devereux et al., Nucl. Acid Res. 12:387–395 (1984). The alignment may include the introduction of gaps in the sequences to be aligned. In addition, for sequences which contain either more or fewer amino acids than the protein shown in FIGS. 6 and 12, it is understood that the percentage of homology will be determined based on the number of homologous amino acids in relation to the total number of amino acids. Thus, for example, homology of sequences shorter than those shown in FIGS. 6 and 12, as discussed below, will be determined using the number of amino acids in the shorter sequence.

NRSF proteins of the present invention may be shorter or longer than the amino acid sequences shown in FIGS. 6 and 12. Thus, in a preferred embodiment, included within the definition of NRSF proteins are portions or fragments of the sequences shown in FIGS. 6 and 12. In particular, fragments including the "zinc fingers" of the sequences shown in FIGS. 6 and 12 are preferred. The fragments may range from about 250 to about 600 amino acids. It should be noted that fragments of transcription factors may exhibit all of the functional properties of the intact molecule (H. Weintraub, et al., Science 251,761–766 (1991); U. Henz, B. Biebel, J. A. Compos-Ortega, Cell 76, 77–88 (1994).

The NRSF proteins and nucleic acids may also be longer than the sequences shown in FIGS. 6 and 12, although the sequences depicted in FIG. 12 are full-length. In particular, human sequences of roughly 1100 amino acids are preferred.

In a preferred embodiment, for example when the NRSF protein is to be used to generate antibodies, the NRSF protein must share at least one epitope or determinant with the full length protein, and preferably with the proteins shown in FIGS. 6 and 12. By "epitope" or "determinant" herein is meant a portion of a protein which will generate and bind an antibody. Thus, in most instances, antibodies made to a smaller NRSF protein will be able to bind to a larger portion or the full length protein. In a preferred embodiment, the epitope is unique; that is, antibodies generated to a unique epitope show little or no cross-reactivity with other proteins. The NRSF antibodies of the invention specifically bind to NRSF proteins. By "specifically bind" herein is meant that the antibodies bind to the protein with a binding constant in the range of at least $10^4$–$10^6$ M$^{-1}$, with a preferred range being $10^7$–$10^9$ M$^{-1}$.

In the case of the nucleic acid, the overall homology of the nucleic acid sequence is commensurate with amino acid homology but takes into account the degeneracy in the genetic code and codon bias of different organisms. Accordingly, the nucleic acid sequence homology may be either lower or higher than that of the protein sequence. Similar to the protein sequence, there may be NRSF nucleic acids which contain additional nucleotides as compared to the sequence shown in FIG. 6, and may contain "overlap" regions with the sequence of FIG. 6. NRSF nucleic acids have homology to the FIG. 6 sequence within the overlap region. The homology of the NRSF nucleic acid sequence as directly compared to the nucleic acid sequences of FIGS. 6 and 12 is preferably greater than about 60%, more preferably greater than about 70% and most preferably greater than 80%. In some embodiments the homology will be as high as about 90 to 95 or 98%.

In one embodiment, the nucleic acid homology is determined through hybridization studies. Thus, for example, nucleic acids which hybridize under high stringency to all or part of the nucleic acid sequences shown in FIGS. 6 and 12 are considered NRSF protein genes. High stringency conditions are generally 0.1×SSC at 37–65° C.

The NRSF proteins and nucleic acids of the present invention are preferably recombinant. As used herein, "nucleic acid" may refer to either DNA or RNA, or molecules which contain both deoxy- and ribonucleotides. The nucleic acids include genomic DNA, cDNA and oligonucleotides including sense and anti-sense nucleic acids. Such nucleic acids may also contain modifications in the ribose-phosphate backbone to increase stability and half life of such molecules in physiological environments.

Specifically included within the definition of nucleic acid are anti-sense nucleic acids. Generally, anti-sense nucleic acids function to prevent expression of mRNA, such that a NRSF protein is not made. An anti-sense nucleic acid hybridizes to the nucleic acid sequences shown in FIGS. 6 and 12 or their complements, but may contain ribonucleotides as well as deoxyribonucleotides. It is to be understood that the anti-sense nucleic acid may be shorter than the full-length gene; that is, the anti-sense nucleic acid need only hybridize to a portion of the complement of the NRSF gene to suppress expression of the NRSF. Preferably, hybridization of the anti-sense nucleic acid to the endogeneous NRSF mRNA forms a stable duplex which prevents the translation of the mRNA and thus the formation of functional NRSF protein. Accordingly, preferably hybridization of the anti-sense nucleic acid prevents initiation of translation, or results in premature termination of translation such that a functional protein or peptide is not made. Alternatively, the anti-sense nucleic acid binds to the complement of the portion of the gene which confers functionality, i.e. DNA binding. The hybridization conditions used for the determination of anti-sense hybridization will generally be high stringency conditions, such as 0.1× SSC at 65° C.

The nucleic acid may be double stranded, single stranded, or contain portions of both double stranded or single stranded sequence. By the term "recombinant nucleic acid" herein is meant nucleic acid, originally formed in vitro, in general, by the manipulation of nucleic acid by endonucleases, in a form not normally found in nature. Thus an isolated NRSF nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it can replicate non-recombinantly, i.e. using the in vivo cellular machinery of the host cell rather than in vitro manipulations; however, such nucleic acids, once produced recombinantly, although subsequently replicated non-recombinantly, are still considered recombinant for the purposes of the invention.

Similarly, a "recombinant protein" is a protein made using recombinant techniques, i.e. through the expression of a recombinant nucleic acid as depicted above. A recombinant protein is distinguished from naturally occurring protein by at least one or more characteristics. For example, the protein may be isolated away from some or all of the proteins and compounds with which it is normally associated in its wild type host. The definition includes the production of a NRSF protein from one organism in a different organism or host cell. Alternatively, the protein may be made at a significantly higher concentration than is normally seen, through the use of a inducible promoter or high expression promoter, such that the protein is made at increased concentration levels. Optionally, the protein may be made in a cell type which usually does not express the NRSF protein, or at a stage in development which is different from the normal or wild-type time of expression. Alternatively, the protein may be in a form not normally found in nature, as in the addition of an epitope tag or amino acid substitutions, insertions and/or deletions. Although not usually considered recombinant, the definition also includes proteins made synthetically.

Also included with the definition of NRSF protein are NRSF proteins from other organisms, which are cloned and expressed as outlined below. In a preferred embodiment, the NRSF proteins are from humans and mice, although NRSF proteins from rats, Xenopus, drosophila, zebrafish and *C. elegans* are also included within the definition of NRSF proteins. It should be noted that the homology of NRSF nucleic acids from different organisms is quite high as demonstrated with Southern blot analysis of the human, mouse and rat genes. The human sequence was used to clone mouse and Xenopus NRSF nucleic acids.

An NRSF protein may also be defined functionally. A NRSF is capable of binding to at least one NRSE, or a consensus NRSE, such as depicted in FIG. 1. By "binding to a NRSE" herein is meant that the NRSF can cause a shift in the electrophoretic molibity of the NRSE in an electrophoretic mobility shift assay as outlined below. It is to be understood that the full length protein is not required for binding to a NRSE, since the partial sequence shown in FIG. 6 is sufficient for binding to an NRSE.

Alternatively, an NRSF may be defined as a protein which is capable of suppressing or silencing the expression of neuronal genes. By "neuronal genes" herein is meant genes which are preferentially expressed in neurons. Preferably, the neuronal gene is not expressed significantly, if at all, in any other types of tissues. Examples of neuronal genes include, but are not limited to, SCG10, NaII channel, synapsin I, brain-derived neurotrophic factor, glycine receptor subunit, N-methyl-D-aspartate receptor, neuronal nicotinic acetylcholine receptor β2 subunit, middle molecular weight neurofilament, neuron-specific β4 tubulin, corticotrophin releasing factor (CRF), calbindin, synaptotagmin-4, transcription factor HES-3, and synaptophysin.

Also included within the definition of a NRSF are amino acid sequence variants. These variants fall into one or more of three classes: substitutional, insertional or deletional variants. These variants ordinarily are prepared by site specific mutagenesis of nucleotides in the DNA encoding the NRSF protein, using cassette mutagenesis or other techniques well known in the art, to produce DNA encoding the variant, and thereafter expressing the DNA in recombinant cell culture as outlined above. However, just as for wild-type NRSF proteins, variant NRSF protein fragments having up to about 100–150 residues may be prepared by in vitro synthesis using established techniques. Amino acid sequence variants are characterized by the predetermined nature of the variation, a feature that sets them apart from naturally occurring allelic or interspecies variation of the NRSF protein amino acid sequence. The variants typically exhibit the same qualitative biological activity as the naturally occurring analogue, although variants can also be selected which have modified characteristics.

While the site or region for introducing an amino acid sequence variation is predetermined, the mutation per se need not be predetermined. For example, in order to optimize the performance of a mutation at a given site, random mutagenesis may be conducted at the target codon or region and the expressed NRSF protein variants screened for the optimal combination of desired activity. Techniques for making substitution mutations at predetermined sites in DNA having a known sequence are well known, for example, M13 primer mutagenesis. Screening of the mutants is done using assays of NRSF activities; for example, mutated NRSF proteins may be tested for binding to NRSEs.

Amino acid substitutions are typically of single residues; insertions usually will be on the order of from about 1 to 20 amino acids, although considerably larger insertions may be tolerated. Deletions range from about 1 to 30 residues, although in some cases deletions may be much larger; for example, biological activity is present with the partial sequence depicted in FIG. 6.

Substitutions, deletions, insertions or any combination thereof may be used to arrive at a final derivative. Generally these changes are done on a few amino acids to minimize the alteration of the molecule. However, larger changes may be tolerated in certain circumstances.

The NRSF protein may also be made as a fusion protein, using techniques well known in the art. Thus, for example, for the creation of monoclonal antibodies, if the desired epitope is small, the NRSF protein may be fused to a carrier protein to form an immunogen. Alternatively, the NRSF protein may be made as a fusion protein to increase expression.

Once the NRSF nucleic acid is identified, it can be cloned and, if necessary, its constituent parts recombined to form the entire NRSF nucleic acid. For example, all or part of the nucleic acids depicted in FIGS. 6 and 12 may be used to clone the full length NRSF nucleic acid from either a cDNA library or from the genome of an organism. This is done using techniques well known in the art. For example, by sequencing overlapping clones both upstream and downstream to the sequence shown in FIG. 6, the entire human cDNA sequence may be elucidated. As outlined above, it appears that the full length cDNA is roughly 4 kilobases long, of which roughly 2 kilobases is shown in FIG. 6. Once isolated from its natural source, e.g., contained within a plasmid or other vector or excised therefrom as a linear nucleic acid segment, the recombinant NRSF nucleic acid can be further used as a probe to identify and isolate other NRSF nucleic acids from other organisms. It can also be used as a "precursor" nucleic acid to make modified or variant NRSF nucleic acids and proteins.

Using the nucleic acids of the present invention which encode NRSF, a variety of expression vectors are made. The expression vectors may be either self-replicating extrachromosomal vectors or vectors which integrate into a host genome. Generally, these expression vectors include transcriptional and translational regulatory nucleic acid operably linked to the nucleic acid encoding the NRSF protein. "Operably linked" in this context means that the transcriptional and translational regulatory nucleic acid is positioned relative to the coding sequence of the NRSF protein in such a manner that transcription is initiated. Generally, this will mean that the promoter and transcriptional initiation or start sequences are positioned 5' to the NRSF coding region. The transcriptional and translational regulatory nucleic acid will generally be appropriate to the host cell used to express the NRSF protein; for example, transcriptional and translational regulatory nucleic acid sequences from Bacillus are preferably used to express the NRSF protein in Bacillus. Numerous types of appropriate expression vectors, and suitable regulatory sequences are known in the art for a variety of host cells.

In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters or hybrid promoters.

Hybrid promoters, which combine elements of more than one promoter, are also known in the art, and are useful in the present invention.

In addition, the expression vector may comprise additional elements. For example, the expression vector may have two replication systems, thus allowing it to be maintained in two organisms, for example in mammalian or insect cells for expression and in a procaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

In addition, in a preferred embodiment, the expression vector contains a selectable marker gene to allow the selection of transformed host cells. Selection genes are well known in the art and will vary with the host cell used.

The NRSF proteins of the present invention are produced by culturing a host cell transformed with an expression vector containing nucleic acid encoding a NRSF protein, under the appropriate conditions to induce or cause expression of the NRSF protein. The conditions appropriate for NRSF protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral systems used in insect cell expression are lytic viruses, and thus harvest time selection can be crucial for product yield.

Appropriate host cells include yeast, bacteria, archebacteria, fungi, and insect and animal cells, including mammalian cells. Of particular interest are *Drosophila melangaster* cells, *Saccharomyces cerevisiae* and other yeasts, *E. coli, Bacillus subtilis*, SF9 cells, C129 cells, 293 cells, Neurospora, BHK, CHO, COS, and HeLa cells, immortalized mammalian myeloid and lymphoid cell lines.

In one embodiment, the NRSF nucleic acids, proteins and antibodies of the invention are labelled. By "labelled" herein is meant that a compound has at least one element, isotope or chemical compound attached to enable the detection of the compound. In general, labels fall into three classes: a) isotopic labels, which may be radioactive or heavy isotopes; b) immune labels, which may be antibodies or antigens; and c) colored or fluorescent dyes. The labels may be incorporated into the compound at any position.

The NRSF proteins and nucleic acids encoding NRSF proteins find use in a number of applications. All or part of the NRSF nucleic acid sequences depicted in FIGS. 6 and 12 may be used to clone longer NRSF sequences, preferably including the initiation and stop codons, and more preferably including any upstream regulatory sequences as well. The NRSF proteins may be coupled, using standard technology, to affinity chromatography columns, for example to purify NRSF antibodies.

In particular, nucleic acids encoding NRSF proteins may be used to disrupt the expression of NRSF proteins within a cell, to allow the cell to express neuronal proteins. For example, NRSF genes containing deletions of significant coding portions may be inserted into the genome of the host, using an integration expression vector and homologous recombination, to disrupt the expression of NRSF protein, thus allowing the expression of neuronal genes. For example, the expression of NRSF in neuronal precursor cells may be eliminated, thus allowing the precursor cells to differentiate into neurons. For example, precursor cells may be removed from a patient, treated with NRSF nucleic acid to suppress the expression of NRSF and thus allow expression of neuronal genes and differentiation into neurons, and then the neurons transplanted back into the patient as needed.

Similarly, anti-sense nucleic acids may be introduced into precursor cells for the same purpose. The anti-sense nucleic acid binds to the mRNA encoding the NRSF and prevent translation, thus reducing or eliminating the NRSF within the cell and allowing differentiation into neurons.

The NRSF proteins may also be used as targets to screen for drugs that inhibit the activity of the NRSF protein, for example in commercial drug development programs. These inhibitory drugs may be used as outlined above to allow differentiation into neurons.

NRSF proteins are also useful to search for additional neuronal genes. For example, putative neuronal genes may be combined with NRSF protein and assayed for binding, for example using a mobility shift assay as described herein. Binding of NRSF to a regulatory portion of a gene indicates a strong possibility of the gene being a neuronal gene.

The NRSF proteins are also useful to make antibodies as well. Both polyclonal and monoclonal antibodies may be made, with monoclonal antibodies being preferred. This is done using techniques well known in the art. The antibodies may be generated to all or part of the NRSF sequence. The antibodies are useful to purify the NRSF proteins of the present invention.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference.

EXAMPLES

Example 1
Isolation of a cDNA Clone Encoding NRSF

In previous work, NRSF binding activity was detected in nuclear extracts from non-neuronal cell lines, such as HeLa cells, but not in neuronal cell lines such as PC12 cells (15) N. Mori, S. Schoenherr, D. J. Vandenbergh, D. J. Anderson, *Neuron* 9, 1–10 (1992). Therefore, to isolate a cDNA clone encoding NRSF, a HeLa cell λgt11 cDNA expression library (the generous gift of Paula Henthorn) was screened according to methods of situ detection of filter-bound DNA-binding proteins [H. Singh, J. H. LeBowitz, A. S. Baldwin, Jr., P. A. Sharp, *Cell* 52, 415 (1988); C. R. Vinson, K. L. LaMarco, P. F. Johnson, W. H. Landschulz, S. L. McKnight, *Genes & Dev.* 2, 801 (1988)]. Briefly, the nitrocellulose filters which overlaid the phage plaques were treated with guanidine-HCl and probed as in Vinson et al. (1988) and washed as in Singh et al. (1988). The probe was generated by restriction digest with EcoRI and XhoI of a plasmid containing three Na33 oligonucleotides inserted into the HindIII site of pBluescript and was labeled using [α-$^{32}$P] dATP and dTTP and Klenow fragment. The correct fragment was isolated by PAGE and was further purified using Elutip chromatography (Schleicher and SCHuell). Probes containing two copies of the S36 or Sm36 were isolated in the same manner and were used to confirm the DNA-binding specificity of plaques that recognized the Na33 probe. To obtain additional cDNAs, a HeLa cell λZAPII (Stratagene) and a Balbc/3T3 cell EXlog (the generous gift of S. Tactigian and B. Wold) cDNA library were screened using standard hybridization procedures. The nucleotide sequence of both strands of each cDNA was determined by the dideoxy sequencing method using Sequenase version 2.0 (U.S. Biochemicals). The resulting sequences were assembled and analyzed using the GCG [J. D. Devereux, P. Haeberli, O. Smithies, *Nuc. Acids. Res.* 12, 387 (1984)] and BLAST programs [S. F. Altschul, W. Gish, W. Miller, E. W. Myers, D. j. Lipman, *J. Mol. Biol.* 215, 403 (1990)]. The PROSITE data base [A. Bairoch, *Nuc. Acids Res.* 20, 2013 (1992)] was used to search for protein sequence motifs. cDNAs for mouse NRSF were isolated from the Balbc/3T3 library to permit analysis of the expression pattern of NRSF mRNA in the mouse and the rat. The longest cDNA, λM5 shows 81% amino acid sequence identity with the human sequence over the entire clone, and the identity over the zinc finger domain (including the interfinger sequence) is 96% (241/252)(data not shown).

Approximately two million plaques were screened initially using a radiolabeled probe consisting of three tandemly arrayed copies of the NaII NRSE, Na33. The DNA probes for screening the library are referred to as S36, Sm36 and Na33. S36 and Na33 are the NRSE elements present in the SCG10 and NaII channel genes, respectively. Both of these elements have previously been shown to be sufficient to confer silencing activity and are bound by NRSF. The Sm36 sequence contains two point mutations in the S36 sequence and has an approximately 100 fold lower affinity for NRSF. The sequence of the top strand of the oligonucleotides used for library screening and EMSAs are given below. The upper case sequences represent actual genomic sequence, the lower case sequences are used for cloning purposes.

S36: agctGCAAAGCCATTTCAGCACCACG-GAGAGTGCCTCTGC (SEQ ID NO:51);
Na33: ageATTGGGTTTCAGAACCACGGACAG-CACCAGAGTa (SEQ ID NO:52);
Syn: agettATGCCAGCTTCAGCACCGCGGA-CAGTGCCTTCCa (SEQ ID NO:53);
BDNF: agettAGAGTCCATTCAGCACCTTGGA-CAGAGCCAGCGGa (SEQ ID NO:54);
Ets: agettGCGGAACGGAAGCGGAAACCGa (SEQ ID NO:55).

Positive plaques from this screen were tested further for sequence specific DNA-binding by an additional screen with probes containing the SCG10 NRSE S36 or the mutated NRSE, Sm36 (15) N. Mori, S. Schoenherr, D. J. Vandenbergh, D. J. Anderson, *Neuron* 9, 1–10 (1992). One phage was identified, λH1, that like native NRSF bound both the S36 and the Na33 probes but not the control Sm36 probe.

As an additional test of the authenticity of the cDNA clone, the DNA-binding specificity of its encoded protein was compared to that of native NRSF present in HeLa cell nuclear extracts using an electrophoretic mobility shift assay (EMSA). To generate recombinant protein, the λH1 insert was subcloned into the EcoRI site of pRSET B (Invitrogen), which provided an in-fromae start codon, a poly-histidine tag, and a T7 promoter, Recombinant λH1 was produced by in vitro transcription from linearized plasmid and in vitro translation using a rabbit reticulocyte lysate according to manufacturer's protocol (Promega). Mobility shift assays were performed as described except 0.5 µg supercoiled plasmid and 10 µg of BSA were included in each reaction. This mixture was incubated for 10 minutes on ice. Labeled probe (0.3 ng) in then added to the reaction, followed by a 10 minute incubation at room temperature. Probes were labeled and isolated as described above, and unlabeled competitors were single copy, double-strand oligonucleotides added at the indicated molar excess. Electrophoresis was performed on a 4% polyacrylamide gel (30: 0.8% acrylamide:bis) in 0.25×TBE and electrophoresed for 2 hr at 10 V/cm at room temperature.

The results indicated that both proteins form complexes with the S36 probe (FIG. 3, lane 1, large arrowhead to left of panel vs. lane 9, small arrowhead to right of panel). The faster mobility of the λH1-encoded protein:DNA complex most likely reflects a difference in molecular weight between the fusion protein and the endogenous factor, as the λH1 cDNA does not encode the full-length protein (see below). The sequence specificity of those complexes was tested by competition experiments using unlabeled, double-stranded oligonucleotide binding sites. The SCG10 (S36) and the NaII channel genes (Na33) NRSEs showed similar ability to compete both the λH1-encoded and the native protein:DNA complexes (FIG. 3, compare lanes 2–5 and 10–13). These complexes, however, were poorly competed by the mutated NRSE (Sm36, lanes 6, 7 and 14, 15), and no competition was seen with a control oligonucleotide containing an Ets factor binding site (lanes 8 and 16) (22) K. Lamarco, C. C. Thompson, B. P. Byers, E. M. Walton, S. L. McKnight, Science 253, 789–792 (1991). The data suggest that the protein encoded by λH1 and native NRSF have similar DNA-binding specificities as measured in this assay.

Immunological Relatedness of Recombinant and Native NRSF

To obtain independent evidence for a relationship between native and recombinant NRSF, a mouse polyclonal antibody was generated against bacterially-expressed NRSF and tested for its ability to interact with native NRSD in an EMSA. The λH1 cDNA was inserted into the ExoRI site of pGEX-1, a prokaryotic glutathione S-transferase fusion expression vector [D. B. Smith and K. S. Johnson, Gene 67,31 (1988)]. GST-λH1 fusion protein was partially purified by isolation of inclusion bodies. The inclusion body preparation was subjected to SDS-PAGE, gel slices containing the fusion protein were excised, mixed with adjuvant, and injected into mice. When the serum titer reached a sufficient level, a mycloma was injected into the peritoneum of the mouse, and a tumor was allowed to develop for 10 days. The polyclonal ascites fluid (Ou et al., J. Immunol. Meth. 165:75 (1993)) induced by this tumor was collected and clarified by centrifugation.

In a positive control experiment, the antibody was able to specifically supershift a portion of the λH1-encoded protein:DNA complex, while a control ascites was not (FIG. 4, lower panel; bracket, lanes 1–4). In HeLa cell nuclear extracts, the same antibody supershifted a portion of native NRSF complex (FIG. 4, upper panel; bracket, lanes 1–4). Furthermore, no supershift was seen with the control ascites (lanes 6–8) nor with several other control ascites (data not shown). The inability to obtain a complete supershift leaves open the possibility that HeLa nuclear extracts may contain multiple NRSE-binding proteins. Nevertheless, the antigenic similarity of the recombinant and native NRSF proteins provides further evidence that the cDNA clone encodes NRSF.

Example 2

Characterization of NRSF

NRSF Interacts with NRSEs in Multiple Neuron-specific Genes

NRSF-encoding cDNA clones were identified by virtue of their ability to bind to two independently-characterized functional NRSEs, one in the SCG10 gene, the other in the NaII channel gene. To determine whether NRSF also interacts with NRSE-like sequences identified in other neuron-specific genes, EMSAs were performed using probes containing potential NRSEs from the synapsin I and brain-derived neurotrophic factor (BDNF) genes. In the case of synapsin I, the NRSE-like sequence has been shown to function as a silencer by cell transfection assays (18) L. Li, T. Suzuki, N. Mori, P. Greengard, Proceedings of the National Academy of Science (USA) 90, 1460–1464 (1993). In the case of BDNF, the element was identified by sequence homology but has not yet been tested functionally (23) T. Timmusk, et al., Neuron 10, 475–489 (1993). Although BDNF is expressed both in neurons and in non-neuronal cells, this expression is governed by two sets of promoters which are separated by 15 kb; one set of the promoters is specifically utilized in neurons (23) T. Timmusk, et al., Neuron 10, 475–489 (1993). Native NRSF from HeLa cells yielded a specific complex of similar size using probes from all four genes (FIG. 5, lanes 1–4). At least a portion of all four of these complexes could be supershifted by the anti-NRSF antibody, and the SCG10 NRSE complex could be competed by oligonucleotides containing NRSEs from the other three genes (data not shown). Furthermore, all four probes also generated specific complexes with recombinant NRSF (FIG. 5, lanes 5–8). These data indicate that both native and recombinant NRSF are able to interact with consensus NRSEs in multiple neuron-specific genes.

NRSEs Occur in Many Neuronal Genes

Using a consensus NRSE derived from the four functionally-defined sequences (see above), the nucleotide sequence database was searched for related sequences. The Genbank database was searched using three different algorithms: Wordsearch and FastA from the GCG sequence analysis program [J. D. Devereux, P. Hacberli, O. Smithies, Necl. Acids Res. 12, 387 (1984)] and Blast [S. F. Altschul, W. Gish, W. Miller, E. W. Myers, D. J. Lipman, J. Mol. Biol. 215, 403 (1990)]. This search identified 13 additional neuronal genes that show, on average, 93% homology to the consensus NRSE (Table 1A). These genes include NMDA, ACh and glycine receptor subunits, neurofilament and neuron-specific tubulin. Moreover, in the six genes cloned from multiple species, both the sequence and intragenic location of the NRSEs are highly conserved (Table 1B). This conservation of sequence and position in non-coding regions (which are frequently quite divergent between species), strongly suggests that these elements are functionally relevant to the transcription of these genes.

These database searches also revealed NRSE-like sequences in several non-neuronal genes (Table 1C). The average percent similarity was only 84%, however, compared to 93% for the neuronal genes. Moreover, the average number of differences from the consensus NRSE is 3 bases for the non-neuronal genes, compared to 1.2 bases for the neuronal sequences. Thus, NRSF may not bind to all of these sequences, particularly those in which intragenic position is not conserved across species. However, we cannot exclude the possibility that NRSF may regulate some non-neuronal as well as neuronal genes.

NRSF cDNAs Encode a Novel Protein with Eight Zinc Fingers

To isolate longer NRSF cDNA clones, multiple cDNA libraries from human, mouse and rat were screened by hybridization with the λH1 clone. Five different cDNA libraries, derived from human HeLa cells, mouse 10T1/2 cells and rat brain were screened by plaque hybridization. The selection of libraries included those made with inserts size-selected for length greater than 4 kb, as the estimated size of the NRSF mRNA on Northern blots is 8–9 kb. No cDNA isolated from any library extended past the 5' end of clone λHZ4, suggesting a possible strong stop to reverse transcriptase. Clones of similar size were isolated from both the human and mouse cDNA libraries.

The sequence of the longest clone obtained, λHZ4 (2.04 kb), is shown in FIG. 6. λHZ4 has an open reading frame throughout its length with no candidate initiating methionine and no stop codon, indicating that the cDNA does not contain the full protein coding sequence for NRSF. Conceptual translation of the DNA sequence revealed that it contains a cluster of eight zinc fingers of the $C_2H_2$ class with interfinger sequences which place NRSF in the GLI-Krüppel family of zinc finger proteins (FIGS. 5A, B) (26) R. Schuh, et al., *Cell* 47, 1025–1032 (1986); (27) J. M. Ruppert, et al., *Molecular and Cellular Biology* 8, 3104–3113 (1988). C-terminal to the zinc fingers is a 174 amino acid domain rich in lysine (26%; 46/174) and serine/threonine (21%; 37/174; FIG. 5A). A database search using the BLAST program did not reveal any sequences identical to λHZ4, indicating that NRSF represents a novel zinc finger protein (28) S. F. Altschul, W. Gish, W. Miller, W. Myers, D. J. Lipman, *Journal of Molecular Biology* 215, 403–410 (1990). However, two different 'expressed sequence tags' likely to represent partial NRSF cDNAs were identified. High stringency Southern blot analysis of human, mouse and rat genomic DNA suggests that NRSF is a single copy gene (data not shown).

Repression of Transcription by NRSF in vivo

To determine if the longest NRSF cDNA encoded a protein with transcriptional repressing activity, this cDNA (λHZ4) was cloned into the mammalian expression vector pCMV. PC12 cells were co-transfected with this NRSF expression construct and various target plasmids. One target plasmid (pCAT3-S36++) contained two copies of the NRSE inserted upstream of the SCG10 promoter, directing transcription of the bacterial chloramphenicol acetyltransferase (CAT) gene. Control target plasmids contained either the proximal SCG10 promoter alone (pCAT3), or this promoter plus a mutant NRSE which cannot bind NRSF in vitro (pCAT3-Sm36) (15) N. Mori, S. Schoenherr, D. J. Vandenbergh, D. J. Anderson, *Neuron* 9, 1–10 (1992).

To express NRSF in transient transfection experiments, the λHZ4 cDNA was inserted into the EcoRI site of pcDNA3-ATG, a modified form of pcDNA3 (invitrogen), a mammalian expression vector containing the cytomegalovirus enhancer and an oligonucleotide which provides a star codon in-frame with λHZ4 and a stop codon in all three reading frames. Transient transfections of PC12 cells were performed essentially as described. Each cotransfection included 5 µg of a reporter plasmid (pCAT3 or pCAT3-S36++), the expression plasmid (pCMV-1HZ4) at the concentrations indicated, pcDNA3-ATG to control for non-specific vector effects, 2 µg of pRSV-lacZ to normalize transfections and pBluescript to bring the total plasmid up to 10 µg. Cells were harvested 48 hr after transfection and processed for CAT and β-galactosidase assays as described [N. Mori, R. Stein, O' Sigmund, D. J. Anderson, *Neuron* 4, 583 (1990)], except CAT assays were quantified using a Molecular Dynamics Phosphor Imager.

In transient, co-transfection experiments with pCAT3-S36++ and increasing amounts of pCMV-HZ4, transcription from the target plasmid was repressed from 11 to 32 fold (FIG. 8A; FIG. 2). In parallel transfections performed with pCAT3 as the reporter plasmid, only a modest decrease (1.5 fold at maximum pCMV-HZ4 concentration) in activity was seen with increasing amounts of pCMV-HZ4 (FIG. 8B); FIG. 2). Similar results were obtained with the target plasmid containing a mutated NRSE (data not shown). These results indicated that the λHZ4 clone contains at least a portion of the domain required for transcriptional repression, and that repression by cloned NRSF in vivo requires binding to the NRSE.

NRSF is Expressed in Neural Progenitors but not in Neurons

Previous work indicated that NRSE-dependent silencing activity and NRSE-binding activity are present only in non-neuronal cell lines and are absent from cell lines of neuronal origin (7) N. Mori, R. Stein, O. Sigmund, D. J. Anderson, *Neuron* 4, 583–594 (1990); (15) N. Mori, S. Schoenherr, D. J. Vandenbergh, D. J. Anderson, *Neuron* 9, 1–10 (1992); (16) R. A. Maue, S. D. Kraner, R. H. Goodman, G. Mandel, *Neuron* 4, 223–231 (1990); (17) S. D. Kraner, J. A. Chong, H. J. Tsay, G. Mandel, *Neuron* 9, 37–44 (1992). The absence of these activities in neuronal cells could reflect a lack of NRSF gene expression; alternatively, NRSF might be expressed but be functionally inactive in neuronal cells. To distinguish between these possibilities, first RNase protection assayswere performed on several rodent neuronal and non-neuronal cell lines. RNase protections were performed as previously described [J. E. Johnson, K. Zimmerman, T. Saito, D. J. Anderson, *Development* 114, 75 (1992)] with minor modifications as indicated. The mouse NRSF riboprobe was created using T7 polymerase and a linearized subclone of the EcoRI-Eco47 III fragment froµ 1 M5 into the EcoRI and SmaI sites of pBluescript-KS. A rat β-actin riboprobe (gift of M-J. Fann and P. Patterson) was included in each reaction as a control for the amount and integrity of the RNA. Total cellular RNA was isolated as a control for the amount and integrity of the RNA. Total cellular RNA was isolated using the acid phenol method [P. Chomcynski, N. Sacchi, *Anal. Biochem.* 162, 156 (1987)].

No NRSF transcripts were detectable in two neuronal cell lines, MAH and PC12 cells, which lack NRSE-binding activity in EMSAs (FIG. 9, lanes 4 and 5; rNRSF). In contrast, several rat cell lines of glial origin and two fibroblast lines expressed NRSF mRNA (FIG. 9, lanes 6–9). This pattern of expression is consistent with NRSFs proposed role as a negative regulator of neuron-specific gene expression in non-neuronal cells. Furthermore, the data imply that the absence of NRSF activity in neuronal cells is not due to functional inactivation of NRSF, but rather to the lack of NRSF expression.

In many parts of the embryonic nervous system, neurons and glia derive from multipotent progenitor cells (29) J. R. Sancs, *Trends Neurosci.* 12, 21–28 (1989); (30) R. D. G. McKay, *Cell* 58, 815–821 (1989); (31) S. K. McConnell, *Ann. Rev. Neurosci.* 14, 269–300 (1991). To determine whether such progenitor cells also express NRSF, in situ hybridization experiments on mouse embryos were performed. The morning of the day of detection of a vaginal plug was designated as embryonic day 0.5. Fixation, embedding, sectioning, preparation of digoxygenin-labeled cRNA probes and in situ hybridization with nonradioactive detection were performed as described [S. J. Birren, L. C. Lo, D. J. Anderson, *Development* 119, 507 (1993)]. Both sense and antisense probes for NRSF were generated from linearized plasmid excised from the λM5 EXlox phage using a Cre recombinase system (Novagen). The antisense SCG10 probe has been described elsewhere [R. Stein, N. Mori, K. Matthes, L. Lo, D. J. Anderson, *Neruon* 1, 463 (1988)].

In transverse sections of E12.5 mouse embryos, NRSF hybridization was detected in the ventricular zone of the neural tube (FIG. 10A, arrow), a region containing mitotically active multipotential progenitors of neurons and glia (32) S. M. Leber, S. M. Breedlove, J. R. Sanes, *J. Neurosci.* 10, 2451–2462 (1990) which do not express SCG10 mRNA (compare FIG. 10B, arrow). In contrast, the adjacent marginal zone of the neural tube which contains SCG10 positive neurons (FIG. 10B) was largely devoid of NRSF expression (FIG. 10A). A similar complementarity of NRSF and SCG10 expression in the neural tube was detected at E13.5 (FIGS. 10C, D; arrows), when the marginal zone has expanded. NRSF mRNA was also detected in the ventricular zone of the forebrain (FIG. 11B, arrowhead).

In the peripheral nervous system, NRSF mRNA was absent or expressed at low levels in sympathetic and dorsal root sensory ganglia (DRG) at E13.5 (FIG. 10C, small and large arrowheads) whereas these ganglia clearly expressed SCG10 mRNA (FIG. 10D, small and large arrowheads). At E12.5, the DRG appeared to express higher levels of NRSF mRNA than the marginal zone of the neural tube (FIG. 10A, arrowheads). This NRSF expression may derive from undifferentiated neural crest cells that are present in DRG at these early developmental stages. Taken together, these data suggest that NRSF is expressed by undifferentiated neuronal progenitors but not by differentiated (SCG10+) neurons in vivo.

Widespread Expression of NRSF in Non-neural Tissues

Previous experiments in transgenic mice suggested that the NRSE is required to prevent SCG10 expression in multiple non-neural tissues throughout development (8) C. W. Wuenschell, N. Mori, D. J. Anderson, *Neuron* 4, 595–602 (1990). To determine whether this broad requirement for the NRSE element is reflected in a broad expression of NRSF, we examined its expression in non-neuronal tissues by in situ hybridization experiments. These experiments revealed NRSF mRNA expression in many non-neural tissues such as the adrenal gland, aorta, genital tubercle, gut, kidney, lung, ovaries, pancreas, parathyroid gland, skeletal muscle, testes, thymus, tongue, and umbilical cord (FIGS. 11A, B and data not shown). NRSF mRNA was also detected in a variety of adult non-neuronal tissues by RNase protection (data not shown). This broad expression pattern is consistent with a role for NRSF as a ncar-ubiquitous negative regulator of neuron-specific gene expression.

NRSF Coordinately Represses Multiple Neuron-specific Target Genes

The present finding that many neuron-specific genes are coordinately repressed by a common silencer factor stands in apparent contrast to the cases of most other tissue-specific genes studied previously in higher vertebrates. In these cases, repression in non-expressing tissues is accomplished by both the absence of lineage-specific enhancer factors (12) P. Mitchell, R. Tjian, *Science* 245, 371–378 (1989); (13) P. F. Johnson, S. L. McKnight, *Annu. Rev. Biochem.* 58, 799–839 (1989), and by assembly into transcriptionally-inactive chromatin (43) H. Weintraub, *Cell* 42, 705–711 (1985). While silencer factors have been implicated in the regulation of other cell type-specific genes in higher vertebrates, they appear to function primarily to achieve differential expression between closely-related cell types or developmental stages using common lineage-specific enhancers (35) A. Winoto, D. Baltimore, *Cell*, 59, 649–665 (1989); (36) S. A. Camper, S. M. Tilghman, *Genes Dev.* 3, 537–546 (1989); (37) M. Sheng, M. E. Greenberg, *Neuron* 4, 477–485 (1990); (38) P. Savagner, T. Miyashita, Y. Yamada, *J. Biol. Chem.* 265, 6669–6674 (1990); (39) R. Shen, S. K. Goswami, E. Mascareno, A. Kumar, M. A. Q. Siddiqui, *Mol. Cell. Biol.*, 11, 1676–1685 (1991); (40) S. Sawada, J. D. Scarborough, N. Killeen, D. R. Littman, *Cell* 77, 917–929 (1994). In contrast, the coordinate cell type-specific silencing mediated by NRSF seems more analogous to MATα2 in yeast, which coordinates repression of multiple a-specific genes in α cells (41) I. Herskowitz, *Nature* 342, 749–757 (1989), or to the Drosophila Polycomb genes, which negatively regulate several homeotic genes (42) R. Paro, *Trends in Genetics* 6, 416–421 (1990). The identification of NRSF suggests that coordinate repression of cell-type specific genes may be an alternative mechanism for achieving the differential expression of cell type- or lineage-specific genes in higher vertebrates.

Possible Role of NRSF in Neurogenesis

In other systems, positive-acting transcription factors that coordinately regulate multiple lineage-specific target genes have been shown to function as master regulators of cell type determination or differentiation (1) L. M. Corcoran, et al., *Genes and Development* 7, 570–582 (1993); (3) L. Pevny, et al., *Nature* 349, 257–260 (1991); (33) H. Weintraub, et al., *Science* 251,761–766 (1991); (44) S. Li, et al., *Nature* 347: 528–533 (1990). By analogy, NRSF may play a key role in the selection or expression of a neuronal phenotype. As a first step towards determining the role of NRSF in neurogenesis, the expression pattern of NRSF during embryonic development was examined by in situ hybridization. These data indicate that NRSF is undetectable or expressed at low levels in neurons, but is expressed in regions of the embryonic CNS that contain neuronal precursors. Consistent with this, abundant expression of NRSF mRNA was detected in undifferentiated P19 cells, a murine embryonal carcinoma cell line that can differentiate into neurons when cultured with retinoic acid (unpublished data). The presence of NRSF in neuronal progenitors, together with its proposed coordinate negative regulation of many neuronal genes, suggests that relief from NRSF-imposed repression may be a key event in either neuronal determination or differentiation. In either case, the absence of NRSF mRNA in neurons indicates that this derepression most likely occurs by an extinction of NRSF expression, rather than by its functional inactivation. Such a mechanism implies that neuronal precursors are actively prevented from differentiating until released from this repression by a signal that extinguishes NRSF expression. This idea has intriguing parallels to mechanisms recently shown to underlie neural induction in Xenopus embryos. In that system ectodermal cells are apparently actively prevented from adopting a neural fate by activin, and can undergo neural induction only after a relief from this repression by follistatin, an inhibitor of activin (45) A. Hemmati-Brivanlou, O. G. Kelly, D. A. Melton, *Cell* 77, 283–295 (1994); (46) A. Hemmati-Brivanlou, D. A. Melton, *Cell* 77, 273–281 (1994). It remains to be determined whether the action of follistatin is in any related to the activity or expression of NRSF. In any case, the identification of NRSF provides an opportunity to further understand the control of an apparently central event in neurogenesis.

What is claimed is:

1. A recombinant isolated neuron-restrictive silencer factor (NRSF) protein, comprising a protein selected from the group consisting of proteins having the amino acid sequence shown in FIG. 6 (SEQ ID NO:40), having the amino acid sequence shown in FIG. 12 (SEQ ID NO:50), and functional fragments thereof, wherein a functional fragment is an NRSF protein which
   (a) is at least 250 amino acids in length;
   (b) comprises more than one zinc finger motif;
   (c) is capable of binding to a neuron restrictive silencer element (NRSE); and
   (d) is capable of suppressing or silencing the expression of a neuronal gene.

2. A recombinant isolated nucleic acid encoding a neuron-restrictive silencer factor (NRSF) protein, wherein said nucleic acid encodes a protein having the amino acid sequence shown in FIG. 6 (SEQ ID NO:40) or in FIG. 12 (SEQ ID NO:50).

3. An expression vector comprising transcriptional and translational regulatory nucleic acid operably linked to a nucleic acid having the sequence shown in FIG. 6 (SEQ ID NO:39) or in FIG. 12 (SEQ ID NO:49).

4. A host cell transformed with an expression vector wherein the expression vector comprises a nucleic acid with the sequence shown in FIG. 6 (SEQ ID NO:39) or in FIG. 12 (SEQ ID NO:49).

5. A method of producing an isolated neuron-restrictive silencer factor (NRSF) protein, comprising:
   (a) culturing a host cell transformed with an expressing vector comprising a nucleic acid encoding a neuron-restrictive silencer factor (NRSF) protein, wherein the protein is selected from the group consisting of proteins having the amino acid sequence shown in FIG. 6 (SEQ ID NO:40), having the amino acid sequence shown in FIG. 6 (SEQ ID NO:50), and functional fragments thereof, wherein a functional fragment encodes an NRSF protein which
      (i) is at least 250 amino acids in length;
      (ii) comprises more than one zinc finger motif;
      (iii) is capable of binding to a neuron restrictive silencer element (NRSE); and
      (iv) is capable of suppressing or silencing the expression of a neuronal gene; and
   (b) expressing said nucleic acid to produce a neuron-restrictive silencer factor (NRSF) protein, and
   (c) recovering said protein.

* * * * *